(12) United States Patent
Tegels

(10) Patent No.: US 9,895,144 B2
(45) Date of Patent: Feb. 20, 2018

(54) CIRCUMFERENTIALLY LOCATED SUTURE RELEASE MECHANISM FOR VASCULAR CLOSURE DEVICE

(75) Inventor: Zachary J. Tegels, Minneapolis, MN (US)

(73) Assignee: TERUMO PUERTO RICO, L.L.C., Caguas, PR (US)

( * ) Notice: Subject to any disclaimer, the term of this patent is extended or adjusted under 35 U.S.C. 154(b) by 1108 days.

(21) Appl. No.: 14/123,823

(22) PCT Filed: Jun. 7, 2012

(86) PCT No.: PCT/US2012/041202
§ 371 (c)(1),
(2), (4) Date: Jan. 13, 2014

(87) PCT Pub. No.: WO2012/170601
PCT Pub. Date: Dec. 13, 2012

(65) Prior Publication Data
US 2014/0188160 A1  Jul. 3, 2014

Related U.S. Application Data

(60) Provisional application No. 61/494,322, filed on Jun. 7, 2011.

(51) Int. Cl.
*A61B 17/08* (2006.01)
*A61B 17/00* (2006.01)
*A61B 17/04* (2006.01)

(52) U.S. Cl.
CPC ...... *A61B 17/0057* (2013.01); *A61B 17/0401* (2013.01); *A61B 2017/00623* (2013.01);
(Continued)

(58) Field of Classification Search
CPC ............ A61B 17/0057; A61B 17/0401; A61B 17/0483; A61B 2017/0404;
(Continued)

(56) References Cited

U.S. PATENT DOCUMENTS

| 4,901,938 A | 2/1990 | Cantley et al. |
| 7,618,436 B2 | 11/2009 | Forsberg |

(Continued)

FOREIGN PATENT DOCUMENTS

| WO | 2006124245 A2 | 11/2006 |
| WO | 2010129042 A1 | 11/2010 |

OTHER PUBLICATIONS

PCT International Search Report for PCT International Patent Application No. PCT/US2012/041202, dated Aug. 17, 2012.

*Primary Examiner* — Jonathan Miles
*Assistant Examiner* — Majid Jamialahmadi
(74) *Attorney, Agent, or Firm* — Buchanan Ingersoll & Rooney PC

(57) ABSTRACT

A tissue puncture closure device includes an anchor, a sealing plug, a filament, a compaction member assembly, a spool, a stop feature, a driving plate, and a release member. The filament attaches the sealing plug to the anchor. The compaction member assembly applies an axially directed compressive force to compact the sealing plug toward the anchor. The spool has a portion of the filament wound thereon. The stop feature is coupled to the spool. The driving plate is connected to the spool and arranged to apply a force to a proximal end of the compaction member assembly upon rotation of the driving plate to advance the compaction member assembly. The release member is operable from a first position contacting the stop feature to limit rotation of the spool, and a second position out of contact with the stop feature to permit rotation of the spool.

17 Claims, 18 Drawing Sheets

(52) U.S. Cl.
CPC ............... *A61B 2017/00654* (2013.01); *A61B 2017/0496* (2013.01)

(58) Field of Classification Search
CPC .... A61B 2017/0414; A61B 2017/0417; A61B 2017/0496
USPC ........................................................ 606/213
See application file for complete search history.

(56) References Cited

U.S. PATENT DOCUMENTS

| 7,618,438 | B2 | 11/2009 | White et al. |
| 2003/0204195 | A1 | 10/2003 | Keane et al. |
| 2005/0085851 | A1 | 4/2005 | Fiehler et al. |
| 2007/0032823 | A1* | 2/2007 | Tegg .................. A61B 17/0057 606/232 |
| 2010/0286727 | A1* | 11/2010 | Terwey .............. A61B 17/0057 606/213 |
| 2011/0077671 | A1 | 3/2011 | Ortiz et al. |

\* cited by examiner

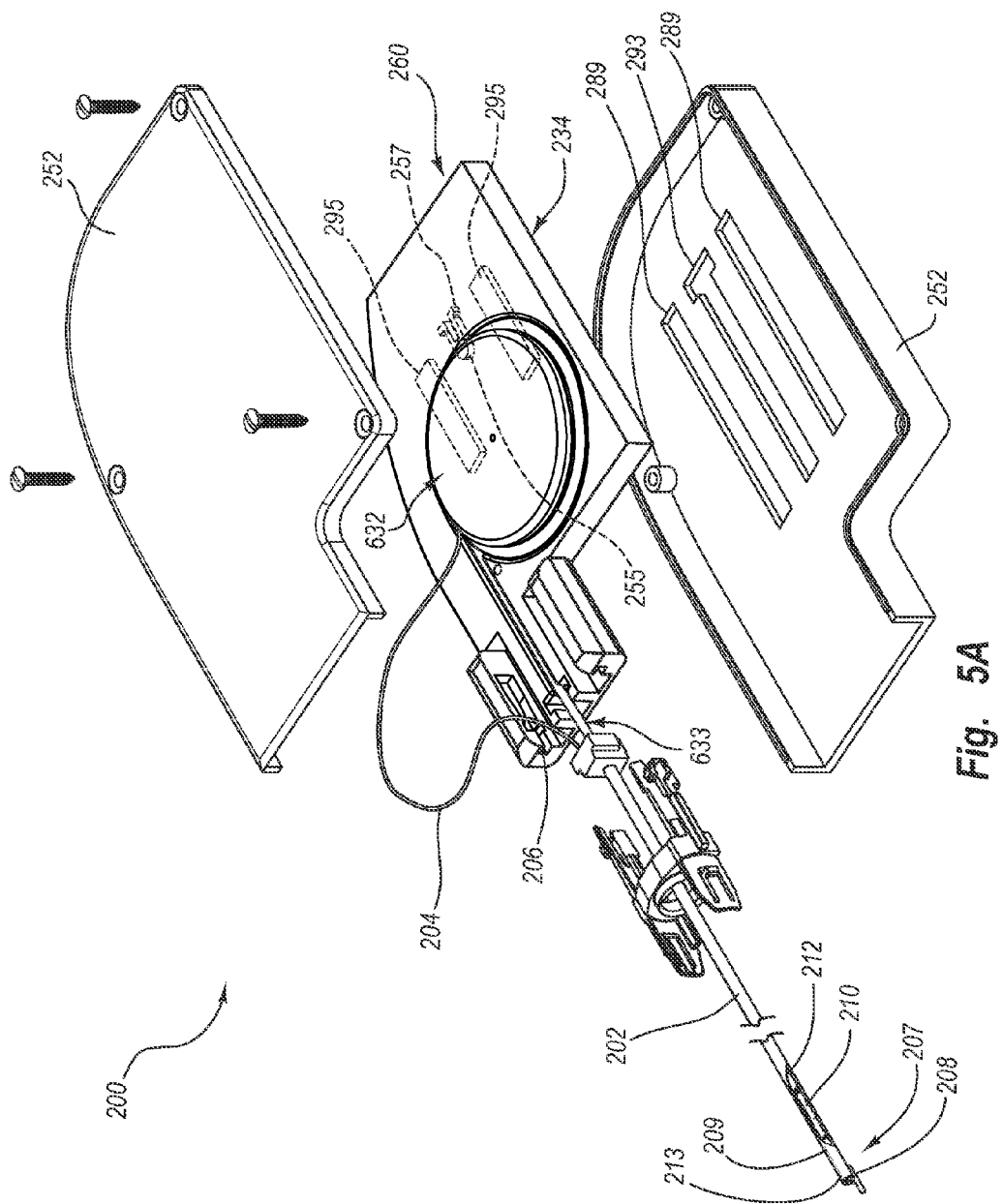

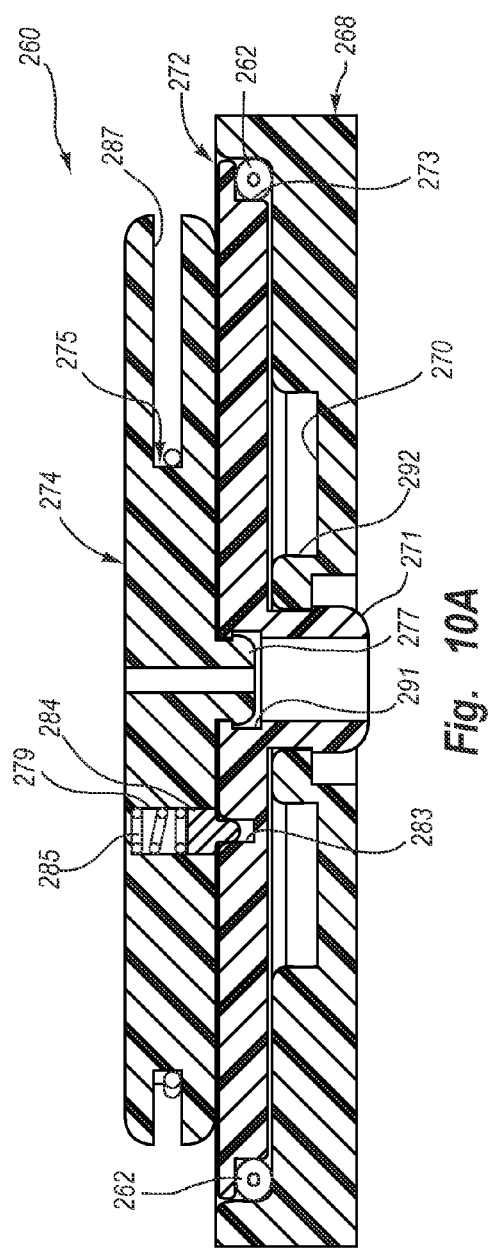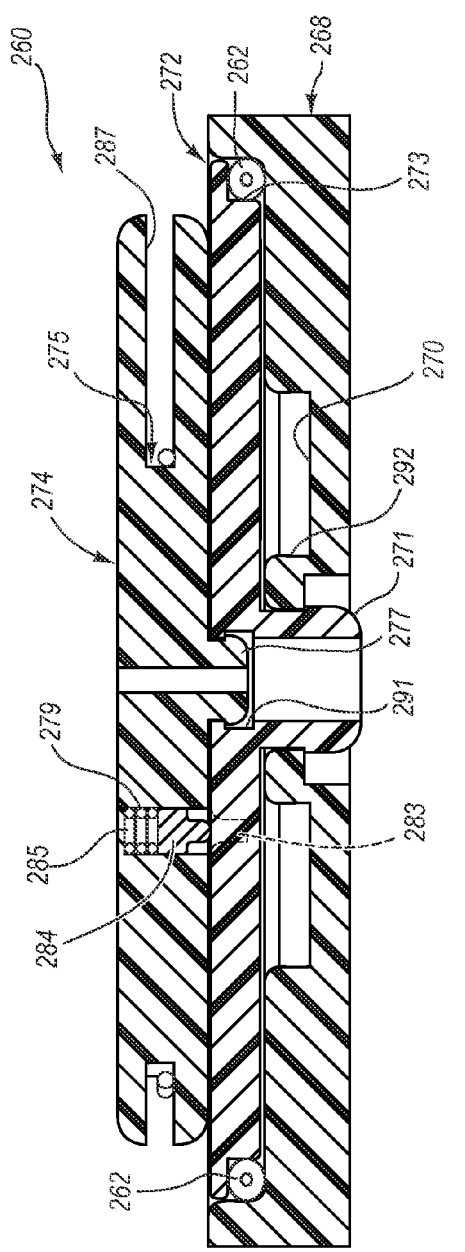

CIRCUMFERENTIALLY LOCATED SUTURE RELEASE MECHANISM FOR VASCULAR CLOSURE DEVICE

RELATED APPLICATION

This claims the benefit of U.S. Provisional Application No. 61/494,322, filed 7 Jun. 2011, which is hereby incorporated by reference herein in its entirety.

TECHNICAL FIELD

The present disclosure relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

Prior closure devices, such as the ones described in the above-mentioned patents, place an anchor within the vessel and position a sealing plug at the tissue puncture site. Deployment of the sealing plug involves ejecting the plug from within a device sheath and compaction down to an outer surface of the tissue puncture using a compaction member. The compaction procedure usually does not commence until the device sheath (within which the compaction tube is located) has been removed so as to expose the compaction tube for manual grasping. Under certain conditions, removal of the sheath prior to compacting the sealing plug may cause the sealing plug itself to be displaced proximally from the tissue puncture, which may hinder subsequent placement of the sealing plug, and may result in only a partial seal and associated late bleeding from the tissue puncture. Advancements are possible for the mechanism that deploys and compacts the sealing plug at the site of a tissue puncture.

Typically, the sealing plug and anchor are connected together with a suture that is also connected to the mechanism that deploys the anchor and sealing plug. Tension in the suture is usually released after compacting the sealing plug to permit disconnection of the suture from the deployment mechanism. Improvements are also possible for the devices and methods used to release the suture from the deployment mechanism.

SUMMARY

The present disclosure meets the above-described needs and others. Specifically, the present disclosure provides methods and systems for closing internal tissue punctures. However, unlike prior systems, the present disclosure provides automatic compaction to a sealing plug as the closure device is retracted. In addition, the present disclosure allows the automatic compaction system to disengage, facilitating full retraction of the closure device and easy separation of the sealing plug from the remainder of the closure device.

In one of many potential embodiments, the present disclosure is directed to a tissue puncture closure device that includes an anchor, a sealing plug, a filament, a compaction member assembly, a spool, a stop feature, a driving plate, and a release member. The filament slidingly attaches the sealing plug to the anchor. The compaction member assembly is disposed adjacent the sealing plug and structured and arranged to apply an axially directed compressive force to automatically compact the sealing plug toward the anchor. The compaction member assembly has a distal end and a proximal end. The spool has a portion of the filament wound thereon. The stop feature is coupled to the spool. The driving plate is connected to the spool and arranged to contact and apply a force to the proximal end of the compaction member assembly upon rotation of the driving plate to advance the compaction member assembly. The release member is operable from a first position contacting the stop feature to limit rotation of the spool, and a second position out of contact with the stop feature to permit rotation of the spool.

The compaction member assembly may include a compaction tube and a coil, wherein the coil is structured and arranged to apply an axially directed compressive force to the compaction tube to drive the compaction tube to automatically compact the sealing plug toward the anchor. The spool may include a cam surface portion, wherein a portion of the filament is wrapped around the cam surface portion, and unwinding the filament from the cam surface portion applies a variable rotation force to the driving plate.

The driving plate may include a recess having a contoured shape, and at least a portion of the coil is positioned in the recess. The stop feature may be a protrusion extending from the spool. The release member may be configured to rotate into and out of contact with the stop feature. The compaction member assembly may include a compaction tube and a coil member arranged end-to-end. The compaction tube may define the distal end of the compaction member assembly and the coil may define the proximal end of the compaction member assembly.

The stop feature may be mounted to the driving plate, and the driving plate may be connected to the spool. The tissue puncture closure device may further include a release member stop configured to hold the release member in the first position, and a housing sized to enclose the spool and driving plate. The release member may be operable from outside of the housing.

Another aspect of the present disclosure relates to a tissue puncture closure device for partial insertion into and sealing of a tissue puncture in an internal tissue wall accessible through a percutaneous incision. The tissue puncture closure device includes an anchor, a sealing plug, a filament, a compaction assembly, a storage spool, and a release member. The anchor is on a distal side of the internal tissue wall. The sealing plug is disposed on a proximal side of the internal tissue wall. The filament is connected to and anchored at a distal end to the anchor and sealing plug for slideably cinching the anchor and sealing plug together about the tissue puncture. The sealing plug is slideably disposed on the filament proximal to the anchor. The compaction assembly is disposed on the filament and arranged to compact the sealing plug along the filament distally toward the anchor. The storage spool has a proximal end of the filament wound thereon. The release member is configured to resist rotation of the storage spool after partial unwinding of the filament from the storage spool, and operable into a release position that permits further unwinding of the filament from the storage spool without further compacting the sealing plug.

The tissue puncture closure device may further include a driving plate connected to and arranged coaxially with the storage spool. The driving plate may be configured to contact the compaction assembly to advance the compaction assembly. The tissue puncture closure device may further include a housing within which the storage spool is housed, wherein the release member includes a first portion that extends or is accessible from outside of the housing and a second portion that rotates into and out of contact with the storage spool.

The storage spool may include a stop feature arranged to contact the release member, the stop feature protruding from a surface of the storage spool. The storage spool may include a cam surface portion about which the proximal end of the filament is wound. The storage spool may apply a variable rotational force to the compaction assembly when the filament unwinds from the cam surface portion. The driving plate may include a stop feature arranged to contact the release member.

A further aspect of the present disclosure is directed to a method of sealing a tissue puncture in an internal tissue wall of a vessel accessible through a percutaneous incision. The method includes providing a closure device having an anchor, a sealing plug, a filament slidingly attaching the sealing plug to the anchor, a compaction member assembly, a spool having a portion of the filament wound thereon, a driving plate, and a release member. A distal end of the compaction member assembly is disposed adjacent to the sealing plug, and a proximal end of the compaction member assembly is in contact with the driving plate. The driving plate is connected to the spool. The method also includes inserting the anchor through the tissue puncture, and withdrawing the closure device from the tissue puncture with the anchor positioned within the vessel. Withdrawing the closure device rotates the spool into contact with the release member, and rotating the spool rotates the driving plate to drive the compaction member assembly and compact the sealing plug toward the anchor. The method further includes actuating the release member to remove the release member from contact with the spool to permit further rotation of the spool without further compacting of the sealing plug toward the anchor.

Rotating the spool into contact with the release member provides a tactile or audible feedback as an indicator to an operator of the closure device that compacting of the sealing plug is complete. The spool may include a stop protrusion, and actuating the release member includes rotating the release member into and out of contact with the stop protrusion. Actuating the release member may include rotating the release member about an axis arranged perpendicular to a direction of compacting the sealing plug toward the anchor.

Additional advantages and novel features of the invention will be set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 5A is a partially exploded top perspective view of a tissue puncture closure device with an automatic compaction or driving mechanism according to one embodiment of the present disclosure.

FIG. 10A is cross-sectional view of the driving mechanism of FIG. 6 taken along cross-section indicators 10A-10A with a driving plate and spool connected together.

FIG. 10B shows the driving mechanism of FIG. 10A with the driving plate and spool disconnected to permit relative rotation.

Throughout the drawings, identical reference numbers designate similar, but not necessarily identical, elements.

DETAILED DESCRIPTION

Figure 1:
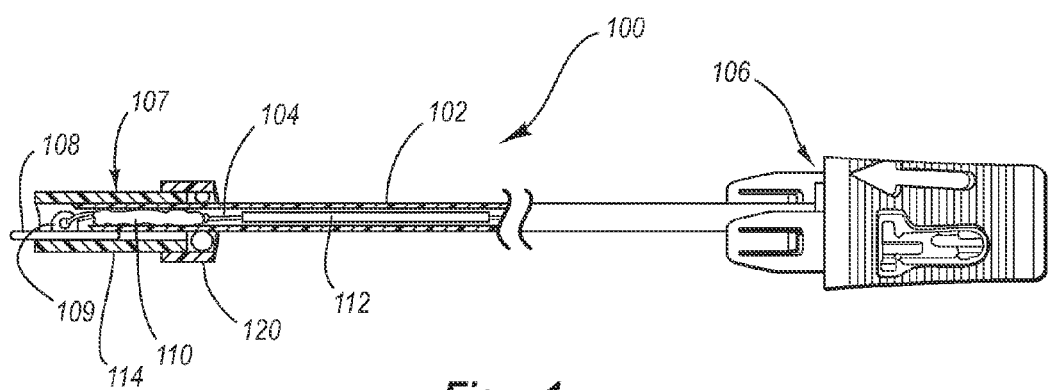
FIG. 1 is a partial cut-away view of a tissue closure device according to the prior art.

As mentioned above, vascular procedures are often conducted throughout the world and involve access to an artery through a puncture. Most often, the artery is a femoral artery. To close the puncture following completion of the procedure, many times a closure device is used to sandwich the puncture between an anchor and a sealing plug. However, sometimes the sealing plug is difficult to eject from the sealing device and may not properly seat against an exterior situs of the arteriotomy. If the plug does not seat properly against the arteriotomy, there is a potential for prolonged bleeding. The present disclosure describes methods and apparatus that facilitate sealing plug ejection and proper placement of the sealing plug. While the vascular instruments shown and described below include procedure sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims.

As used in this specification and the appended claims, the term "compact" or "compacting" is used broadly to mean any type of tamping (i.e., packing down by one or a succession of blows or taps, or smooth, steady pressure, or the like), compacting, or compressing. "Engage" and "engageable" are also used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

Referring to FIGS. 1-4, a vascular puncture closure device 100 is shown according to the prior art. Some example closure devices are disclosed in U.S. Pat. Nos. 7,931,670, 7,618,438 and 7,618,436, which references are incorporated in their entireties by this reference. The closure device 100 includes a carrier tube 102 with a filament or suture 104 extending at least partially therethrough. The closure device 100 also includes a first or proximal end 106 and a second or distal end 107. An anchor 108 is positioned external to the second or distal end 107 of the carrier tube 102. The anchor may be elongated, stiff, low profile member having an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound chemically. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4).

The carrier tube 102 typically includes a compaction member 112 disposed therein. The compaction member 112 is slidingly mounted on the suture 104 and may be used by an operator to compact the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
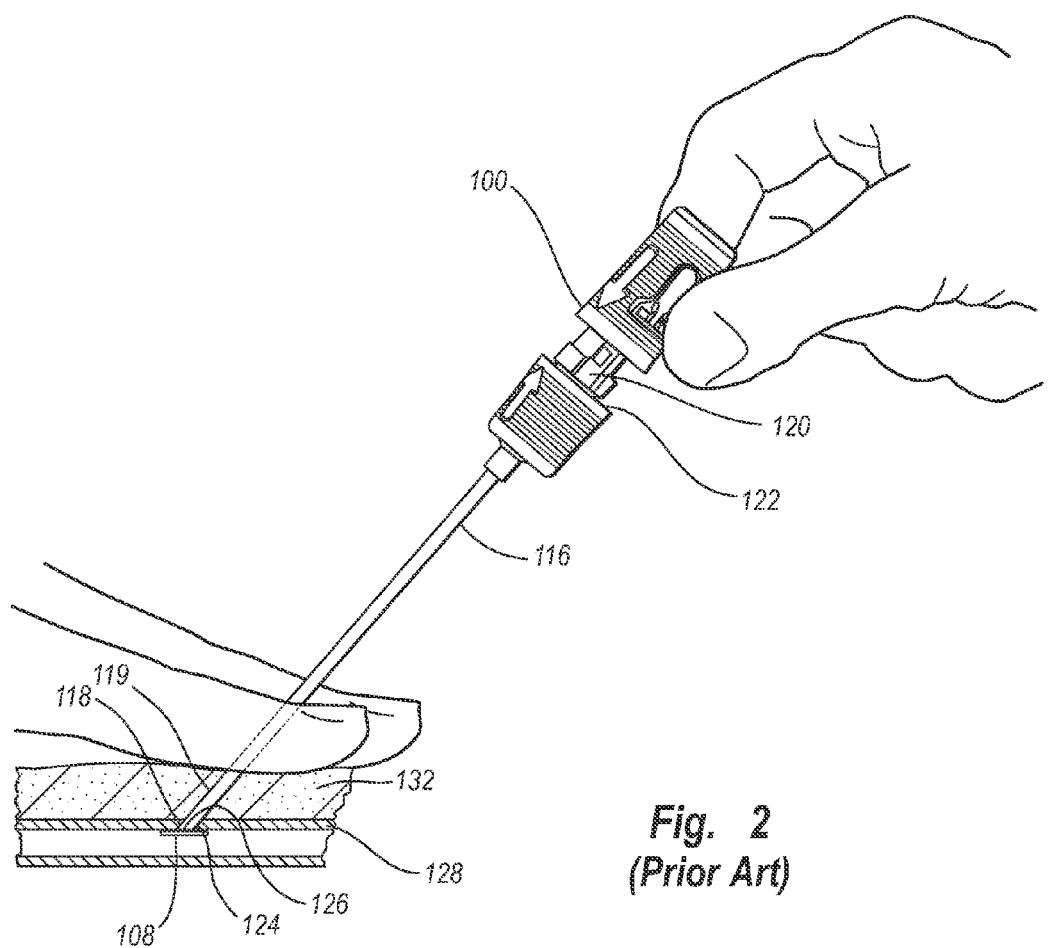
FIG. 2 is a side view of the tissue closure device of FIG. 1 engaged with an artery according to the prior art.
Figure 3:
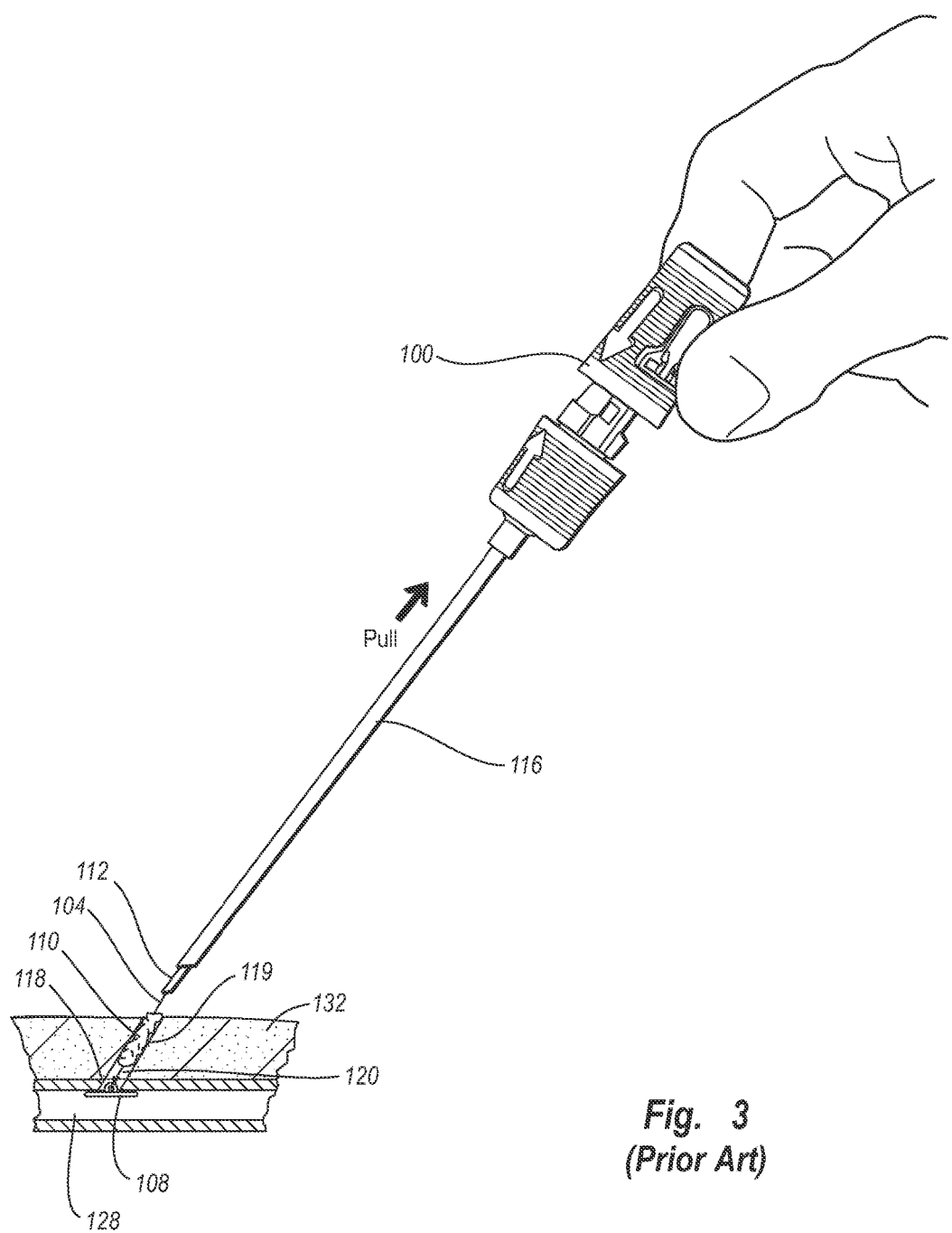
FIG. 3 is a side view of the tissue closure device of FIG. 1 being withdrawn from an artery according to the prior art to deploy a collagen sponge.
Figure 4:
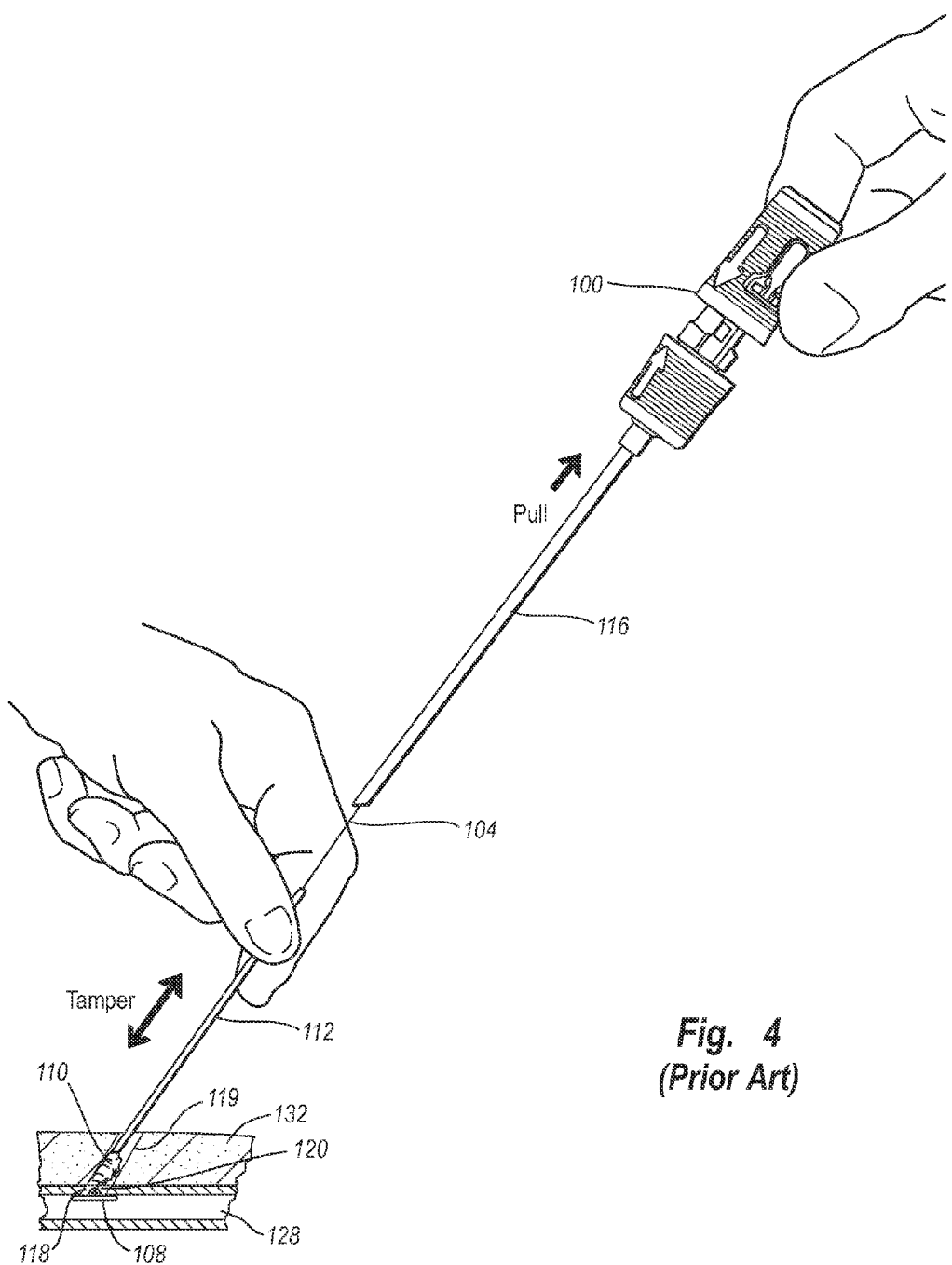
FIG. 4 is a side view of the tissue closure device of FIG. 1 illustrating compaction of the collagen sponge according to the prior art.

The flush arrangement of the anchor 108 and carrier tube 102 allows the anchor 108 to be inserted into a procedure sheath such as insertion sheath 116, shown in FIGS. 2-4, and eventually through an arterial puncture 118. The insertion sheath 116 is inserted through a percutaneous incision 119 and into an artery 128. However, the bypass tube 114 (see FIG. 1) includes an oversized head 120 that prevents the bypass tube 114 from passing through an internal passage of the insertion sheath 116. Therefore, as the closure device 100 is inserted into the insertion sheath 116, the oversized head 120 bears against a surface 122 of insertion sheath 116.

Further insertion of the closure device 100 results in sliding movement between the carrier tube 102 and the bypass tube 114, and releases the anchor 108 from the bypass tube 114. However, the anchor 108 remains in the flush arrangement shown in FIG. 1 following release from the bypass tube 114, limited in movement by the insertion sheath 116.

The insertion sheath 116 may include a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the closure device 100 and the insertion sheath 116 are withdrawn together, ejecting the collagen pad 110 from the carrier tube 102 into the percutaneous incision 119 and exposing the compaction member 112. With the compaction member 112 fully exposed as shown in FIG. 4, the collagen pad 110 is manually compacted, and the anchor 108 and collagen pad 110 are cinched together and held in place with the self-tightening slip-knot on the suture 104. Thus, the tissue puncture is sandwiched between the anchor 108 and the collagen pad 110, thereby sealing the puncture 118. The suture 104 is then cut and the percutaneous incision 119 may be closed. The suture 104, anchor 108, and collagen pad 110 are generally made of resorbable materials and therefore remain in place while the puncture 118 heals.

It may be difficult to eject and compact the collagen pad 110 using the typical closure device 100 described above. The insertion sheath 116 resists deformation as the collagen pad 110 is ejected from the carrier tube and compaction may not commence until the insertion sheath 116 has been removed. Under certain conditions, removal of the insertion sheath 116 prior to compaction of the collagen pad 110 may cause the collagen pad 110 to retract or displace proximally from the puncture 118, creating an undesirable gap between the collagen pad 110 and the puncture 118. The gap may remain even after compaction as shown in FIG. 4, which may result in only a partial seal and bleeding from the puncture 118.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Referring now to FIGS. 5A-5H, an apparatus, for example a tissue puncture closure device 200, is shown according to one embodiment of the present disclosure. The closure device 200 is shown in top and bottom exploded perspective views in FIGS. 5A and 5B. FIGS. 5C-5H illustrate the closure device 200 assembled and inserted through a procedure sheath 216 and into a lumen 232. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the exemplary embodiments below are directed to the sealing off of percutaneous punctures in arteries, such devices have much more wide-spread applications and may be used for sealing punctures or incisions in other types of tissue walls as well. Thus, the sealing of a percutaneous puncture in an artery, shown herein, is merely illustrative of one particular use of the closure device 200 according to principles of the present disclosure.

The closure device 200 includes a first or proximal end portion 206 and a second or distal end portion 207. A carrier tube 202 extends from the proximal end portion 206 to the distal end portion 207 and includes an outlet 213 at the distal end portion 207. The distal end portion 207 may include a slit 209.

The carrier tube 202 may be made of plastic or other material and is designed for insertion through the procedure sheath 216. The procedure sheath 216 (see FIG. 5C) is designed for insertion through a percutaneous incision 219 in a tissue layer 230 and into the lumen 232 (see FIG. 5C). According to FIGS. 5C-5H, the lumen 232 comprises an interior portion of a femoral artery 228.

At the distal end portion 207 of the carrier tube 202 there is an anchor 208 and a sealing plug 210. The anchor 208 of the present embodiment is an elongated, stiff, low-profile member arranged to be seated inside the artery 228 against an artery wall 234 contiguous with a tissue puncture 218 (see FIG. 5C). The anchor 208 may be made of a biologically resorbable polymer. The sealing plug 210 may be formed of a compressible sponge, foam, or fibrous mat made of a non-hemostatic biologically resorbable material such as collagen, and may be configured in any shape so as to facilitate sealing the tissue puncture 218.

Figure 5B:
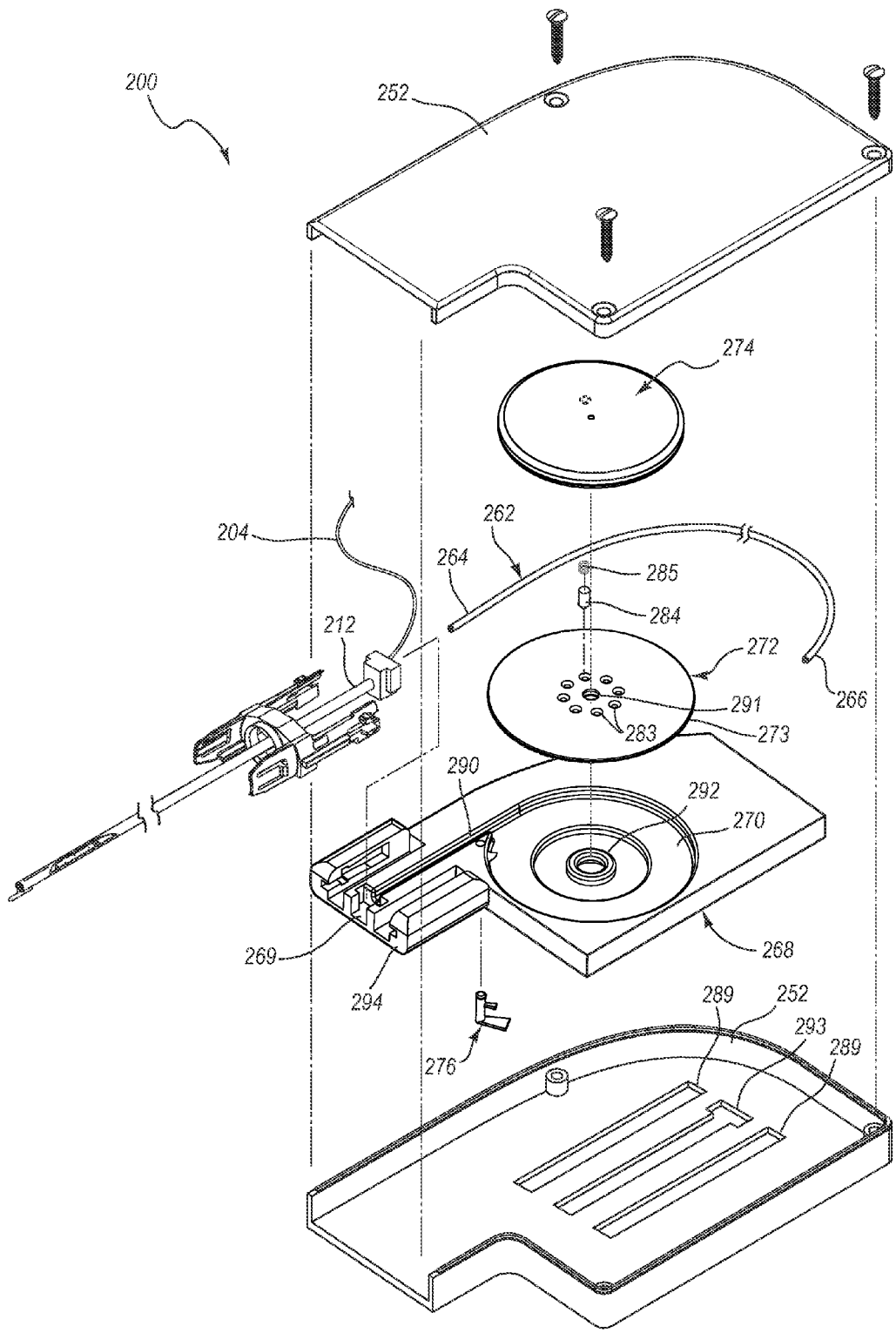
FIG. 5B is an exploded top perspective view of the tissue puncture closure device of FIG. 5A.

The sealing plug 210 and anchor 208 are connected to one another by a connector such as a biologically resorbable filament or suture 204. The anchor 208, the sealing plug 210, and the suture 204 may be collectively referred to as the "closure elements." As shown in FIG. 5A, the anchor 208 is initially arranged adjacent to and exterior of the distal end portion 207 of the carrier tube 202, while the sealing plug 210 is initially disposed within the carrier tube 202. The anchor 208 is shown nested in its low profile configuration along the carrier tube 202 to facilitate insertion into the lumen 232 in FIG. 5A, and deployed with a first surface 236 abutting the artery wall 234 in FIGS. 5B-5G.

The suture 204 extends distally from the proximal end portion 206 of the closure device 200 through the carrier tube 202. The suture 204 may be threaded through one or more perforations in the sealing plug 210, through a hole in the anchor 208, and proximally back toward the carrier tube 202 to the sealing plug 210. The suture 204 is preferably threaded again through a perforation or series of perforations in the sealing plug 210. The suture 204 may also be threaded around itself to form a self-tightening slip-knot. The suture 204 may thus connect the anchor 208 and the sealing plug 210 in a pulley-like arrangement to cinch the anchor 208 and the sealing plug 210 together when the carrier tube 202 is pulled away from the anchor 208 and the sealing plug 210. The anchor 208 and the sealing plug 210 sandwich and lock the anchor and plug together, sealing the tissue puncture 218.

The carrier tube 202 may house a compaction device, such as a compaction tube 212, for advancing the sealing plug 210 along the suture 204 and toward the anchor 208. The compaction tube 212 is shown located partially within the carrier tube 202 and proximal of the sealing plug 210. The compaction tube 212, however, also extends through a handle or housing 252 of the closure device 200. The compaction tube 212 is preferably an elongated tubular or semi-tubular member that may be rigid or flexible and formed of any suitable material. For example, according to one embodiment, the compaction tube 212 is made of polyurethane. The suture 204 extends through at least a portion of the compaction tube 212. For example, as shown in FIGS. 5A-5H, the suture 204 extends along the compaction tube 212 between the proximal and distal end portions 206, 207. However, the suture 204 is not directly connected to the compaction tube 212. Accordingly, the suture 204 and the compaction tube 212 may slide past one another.

According to the embodiment of FIGS. 5A-5H, the suture 204 attaches to an automatic compaction assembly. The automatic compaction assembly may include an automatic driving mechanism 260 or other transducer and the compaction tube 212. The automatic driving mechanism 260 is located within the housing 252 at the first or proximal end portion 206 of the closure device 200. Embodiments of the automatic driving mechanism 260 are described in detail below with reference to FIGS. 6-12, and may be selectively disengageable.

Figure 5C:
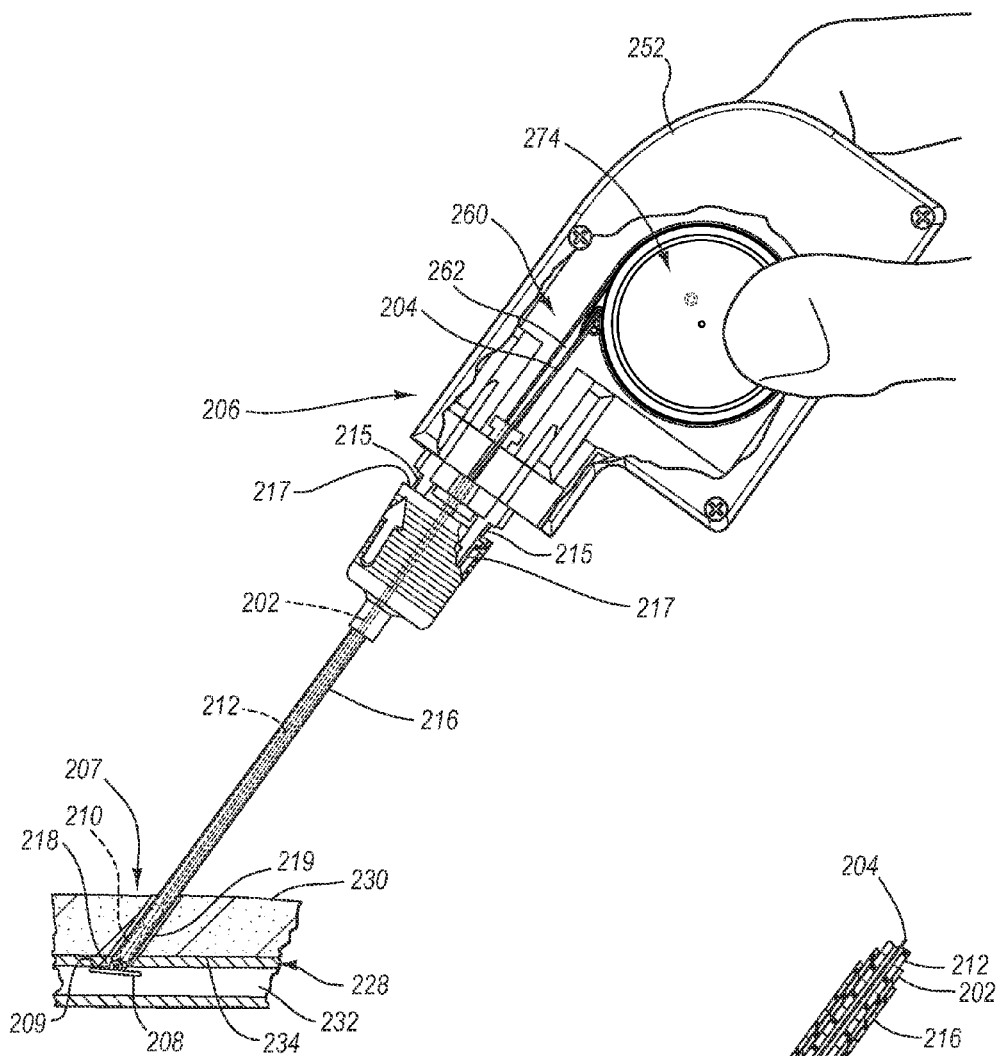
FIG. 5C is a side view of the tissue puncture closure device of FIG. 5A inserted through a procedure sheath and shown engaged with an artery in a first position.
Figure 5D:
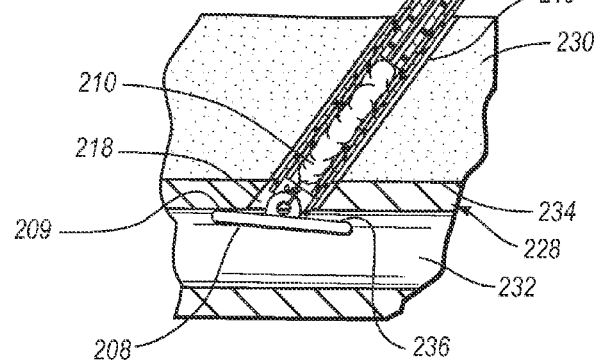
FIG. 5D is a detailed inset of FIG. 5C.

In practice, the carrier tube 202 of the closure device 200 (containing the closure elements described above) is inserted into the procedure sheath 216, which has already been inserted into the artery 228 (see FIGS. 5C-5D). As the closure device 200 and the associated closure elements are inserted into the procedure sheath 216, the anchor 208 passes through and out of the distal end of the procedure sheath 216 and is inserted into the lumen 232. As mentioned above and shown in FIG. 5A, the anchor 208 is initially arranged substantially flush with the carrier tube 202 to facilitate insertion of the anchor 208 through the percutaneous incision 219 and into the lumen 232.

After the anchor 208 passes out of the distal end of the procedure sheath 216, however, it tends to deploy or rotate to the position shown in FIGS. 5C-5D. The closure device 200 may also be partially withdrawn from the procedure sheath 216, catching the anchor 208 on the distal end of the procedure sheath 216 and rotating it to the position shown in FIGS. 5C-5D. However, the closure device 200 preferably includes a pair of biased fingers 215 that are lockingly received by a matching pair of recesses 217 in the procedure sheath 216. The locking arrangement between the biased fingers 215 and matching recesses 217 may fix the position of the housing 252 relative to the procedure sheath 216.

Following deployment of the anchor 208, the housing 252 and the procedure sheath 216 are withdrawn together. Withdrawing the housing 252 causes the anchor 208 to anchor itself within the artery 228 against the artery wall 234. With the anchor 208 anchored within the artery 228 at the tissue puncture 218, further retraction of the housing 252 and procedure sheath 216 tends to pull the sealing plug 210 out from the distal end portion 207 of the carrier tube 202, thereby depositing the sealing plug 210 within the percutaneous incision 219. The slit 209 (see FIG. 5A) in the carrier tube 202 allows the distal end portion 207 of the carrier tube to flex or open, facilitating ejection of the sealing plug 210.

Figures 5E, 5F:
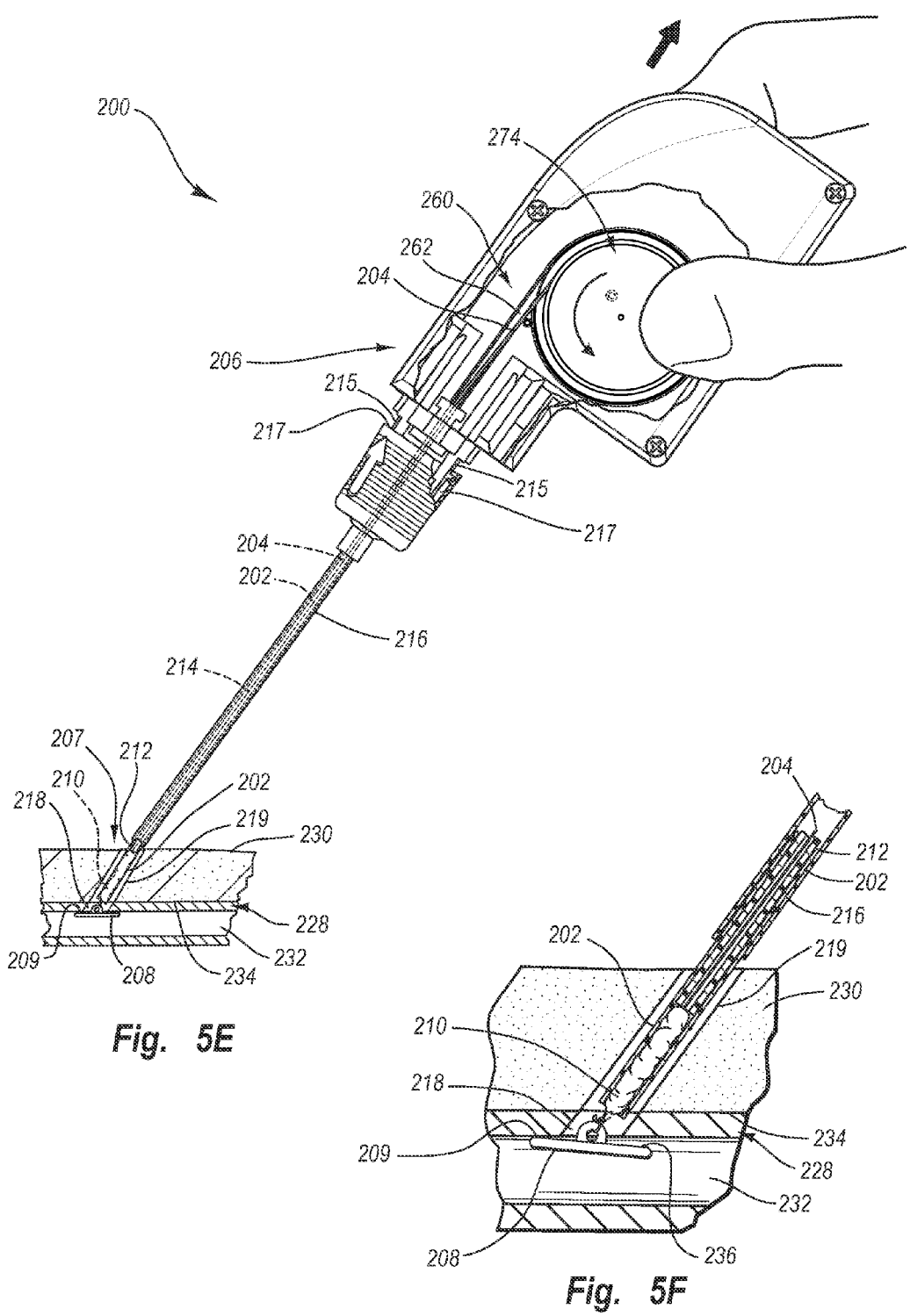
FIG. 5E is a side view of the tissue puncture closure device of FIG. 5A shown engaged with an artery in a second position and being retracted.
FIG. 5F is a detailed inset of FIG. 5E.

Referring to FIGS. 5E-5F, the distal end portion 207 of the carrier tube 202 is exposed (within the percutaneous incision 219) as the housing 252 and the procedure sheath 216 are retracted. The carrier tube 202 may retain its position relative to the tissue puncture 218 until the housing 252 and the procedure sheath 216 have been retracted a predetermined distance. Relative movement between the housing 252/procedure sheath 216 and the carrier tube 202 may be facilitated by a sliding mount arrangement between the automatic driving mechanism 260 and the housing 252. However, some embodiments include the automatic driving mechanism 260 fixed to the housing 252.

As shown by the combination of FIGS. 5C-5H, the automatic driving mechanism 260 (which is attached to the carrier tube 202) may be free floating or displaceable and may slide relative to the housing 252 as the housing 252 and the procedure sheath 216 are retracted. However, the automatic driving mechanism 260 may be initially held in a first position relative to the housing 252 as shown in FIG. 5C. For example, the automatic driving mechanism 260 may comprise a temporary holder such as a stowage detent 255 that helps retain the automatic driving mechanism 260 in a fixed axial position relative to the housing 252 (see FIG. 8). The stowage detent 255 may include a finger 257 with a protrusion to at least temporarily hold the automatic driving mechanism 260 in the first position shown in FIG. 5C, and prevent premature sliding within the housing 252.

Figure 8:
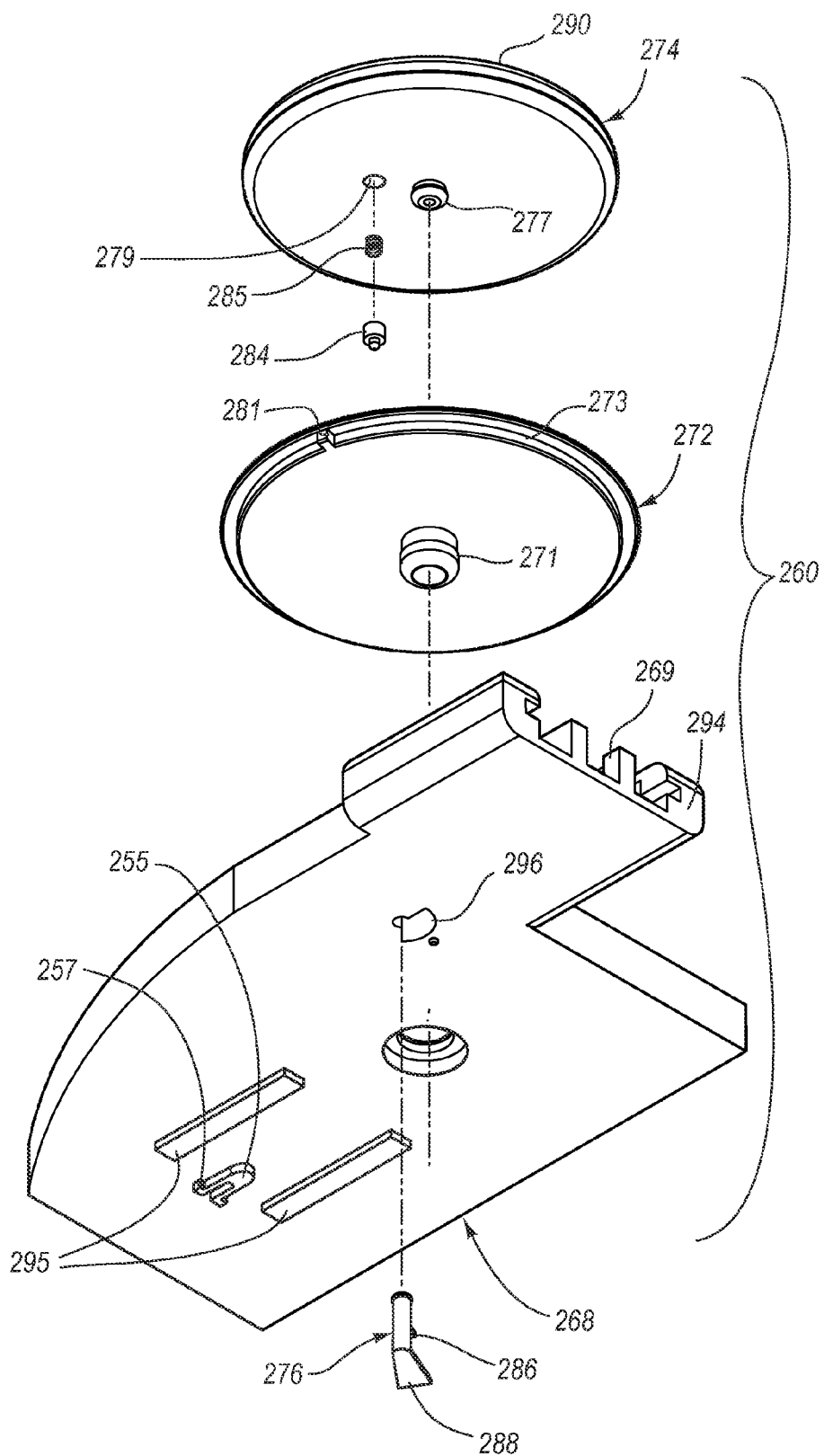
FIG. 8 is an exploded bottom perspective view of the driving mechanism of FIG. 6.

The stowage detent 255 may be positioned at any location, such as along a bottom side of the automatic driving mechanism 260 (see FIG. 8). At least one rail 295 may also be arranged along the bottom side of the automatic driving mechanism 260. The rails 295 and stowage detent 255 may be movable within a set of tracks 289, 293, respectively (see FIG. 5A). The tracks 289, 293 may be positioned on or formed in a portion of the housing 252. The tracks 289 and rails 295 may operate to provide sliding movement of the automatic driving mechanism 260 within the housing 252.

Although the finger 257 tends to hold or temporarily lock the automatic driving mechanism 260 in the first position shown in FIG. 5C, the finger 257 releases within the track 293 when a sufficient predetermined force is applied between the housing 252 and the automatic driving mechanism 260. For example, with the anchor 208 deployed, a retraction force provided by a user to the housing 252 causes the finger 257 to deflect and release. Thereafter, the finger 257 provides very little resistance to sliding movement between the automatic driving mechanism 260 and the housing 252. Accordingly, retraction of the housing 252 may retract the procedure sheath 216 (which is fixedly connected to the housing 252), but the automatic driving mechanism 260 and the carrier tube 202 may slide relative to the housing 252 and therefore remain in position with respect to the tissue puncture 218 as shown in FIG. 5E. The automatic driving mechanism 260 may slide a predetermined distance with respect to the housing 252 until the automatic driving mechanism 260 reaches a stop position within the housing 252. The predetermined distance may be at least long enough to fully expose the slit 209 in the carrier tube 202. The predetermined distance may depend at least in part on the length of the tracks 289, 293 and the rails 295.

Figures 5G, 5H:
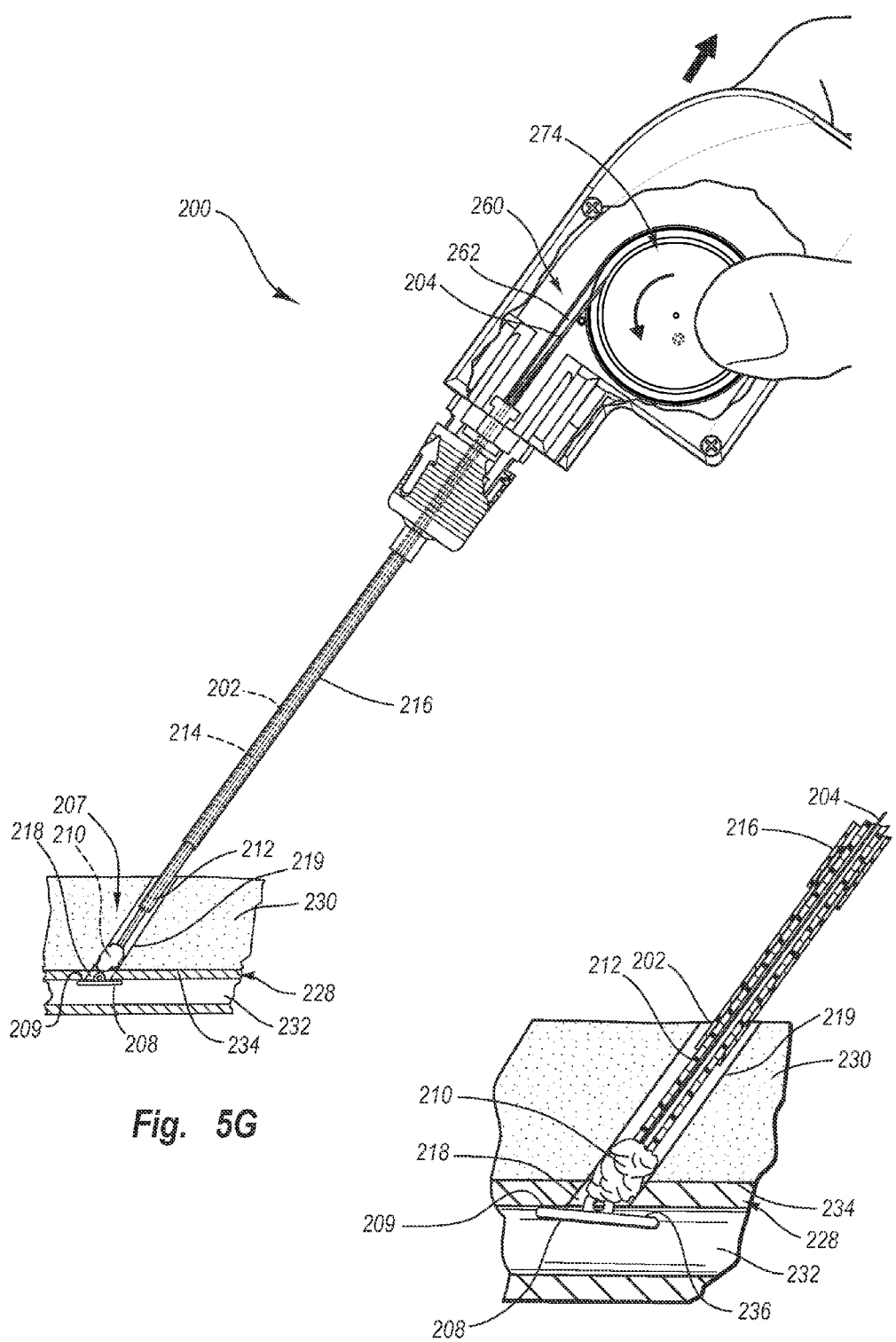
FIG. 5G is a side view of the tissue puncture closure device of FIG. 5A shown engaged with an artery in a third position compacting a sealing plug.
FIG. 5H is a detailed inset of FIG. 5G.
Figure 6:
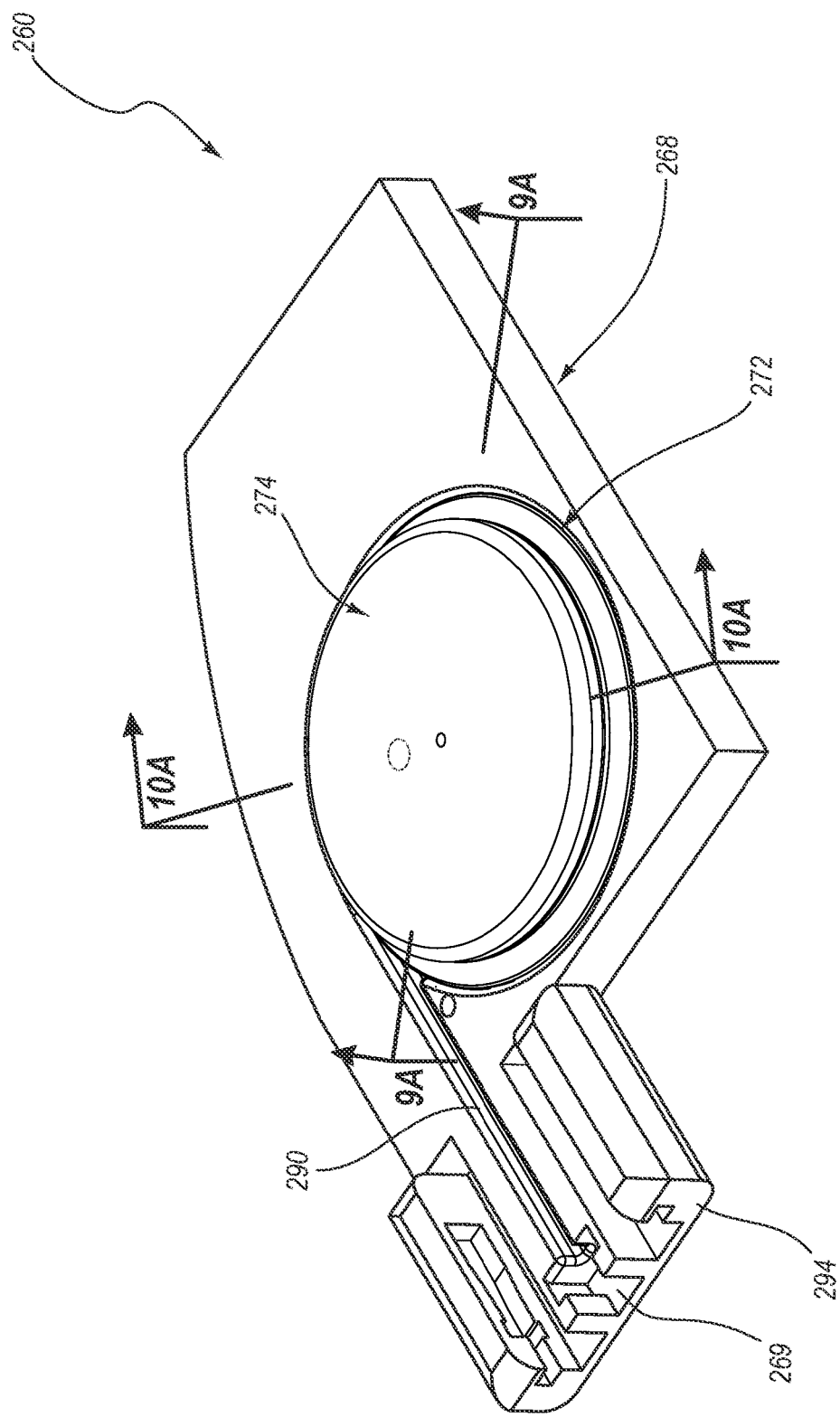
FIG. 6 is illustrates the driving mechanism of FIG. 5A in a top perspective view.
Figure 7:
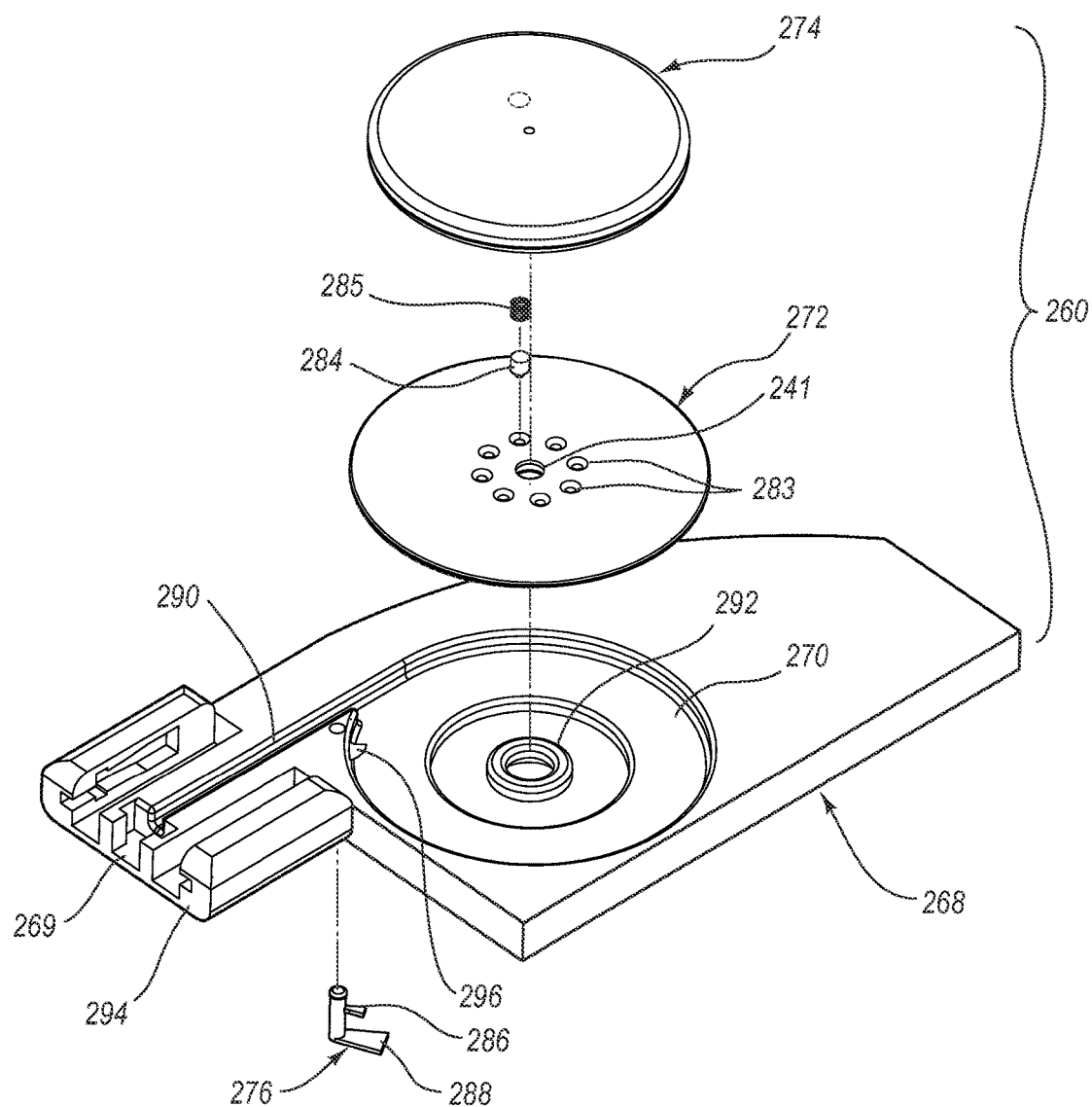
FIG. 7 is an exploded top perspective view of the driving mechanism of FIG. 6.

When the automatic driving mechanism 260 reaches the stop position, further retraction of the housing 252 withdraws the carrier tube 202 as well, ejecting and compacting the sealing plug 210 automatically as shown in FIGS. 5G-5H. Unlike previous closure devices that require a separate, manual compaction procedure following the deposition of the sealing plug 210, the closure device 200 of the present disclosure automatically compacts the sealing plug 210. The sealing plug 210 may be compacted while the carrier tube 202 is being withdrawn, reducing or eliminating any gaps that may otherwise occur between the sealing plug 210 and the tissue puncture 218 in the artery 228.

In addition, by placing tension on or pulling the suture 204 away from the percutaneous incision 219, the suture 204 may cinch and lock (with a slip-knot or the like) together the anchor 208 and the sealing plug 210, sandwiching the artery wall 234 between the anchor 208 and sealing plug 210. The force exerted by the compaction tube 212 and the cinching together of the anchor 208 and sealing plug 210 by the suture 204 also causes the sealing plug 210 to deform radially outward within the percutaneous incision 219 and function as an anchor on the proximal side of the tissue puncture 218 as shown in FIGS. 5F-5G.

The compaction tube 212 is automatically driven toward the sealing plug 210 by the automatic driving mechanism 260. One embodiment of the automatic driving mechanism 260 is shown in detail in FIGS. 5A, 5B and 6-12. The automatic driving mechanism 260 may be selectably disengageable. According to the embodiment of FIGS. 5A, 5B and 6-12, once the automatic driving mechanism 260 reaches the stop position within the housing 252, further retraction of the closure device 200 automatically effects compaction of the sealing plug 210 (see FIGS. 5E-5H).

According to FIGS. 5A, 5B and 6-12, the automatic driving mechanism comprises a coil 262 having a first end 264 and a second end 266. The coil 262 is operatively connected to the sealing plug 210 to automatically compact the sealing plug 210 toward the anchor 208. The coil 262 may abut the compaction tube 212, or the coil 262 may comprise the compaction tube 212. The coil 262 may be semi-flexible, capable of taking the shape of a track, and configured and arranged to provide a compression force to the sealing plug 210.

The automatic driving mechanism 260 may further comprise a block such as plate block 268 that is disposed in the housing 252. The plate block 268 may comprise a connection aperture 269, a recess 270, a coil recess 290, a hub 292, a distal end 294, and a release recess 296. The connection aperture 269 may be used to connect the compaction tube 212 to the plate block 268. The recess 270 may be shaped similarly to a driving plate 272 and may be recessed sufficiently to entirely receive the driving plate 272 and a spool 274. The coil recess 290 is receptive of a least a portion of the coil 262. The coil recess 290 may exhibit a generally straight portion that leads out of the plate block 268.

The hub 292 may be configured to mount the driving plate 272 to the plate block 268. In some arrangements, the hub 292 may be configured to provide a snap-fit connection with the driving plate 272. The hub 292 may provide a bearing surface about which the driving plate 272 rotates.

The distal end 294 may define a surface that contacts an internal surface of the housing 252 to provide the stop position for the automatic driving mechanism 260 within the housing 252. The release recess 296 may be sized to receive at least a portion of a release member 276 that is operable to control some rotational movement of the driving plate 272 and spool 274 relative to the plate block 268 as will be discussed in further detail below.

The driving plate 272 may comprise a disk or circular shape as shown, although the driving plate 272 may include other shapes as well. The driving plate 272 may be rotatably attached to the plate block 268 as shown via a connection protrusion 271. A coil track or groove 273 is defined in the driving plate 272, such as around a peripheral surface of the driving plate 272. A stop feature 281 may be positioned within the coil track 273 or at some other location on the driving plate 272 where the stop feature 281 may be contacted by the release member 276. The stop feature 281 may provide a surface against which a second or proximal end 266 of the coil 262 contacts to transfer rotational forces from the driving plate 272 to the coil 262. In some arrangements, the driving plate 272 includes separate stop features 281 for contact by the release member 276 and the proximal end of the coil 262.

The driving plate 272 may include a connection recess 291 configured to receive a connection feature of the spool 274. In some arrangements, the driving plate 272 and spool 274 may be releasably connected together. The suture 204 is connected to and partially wound about the spool 274. As tension is applied along a length of the suture 204, the spool rotates and causes the driving plate 272 to rotate. The driving plate 272 may rotate at the same angular rate as the spool 274.

The automatic driving mechanism 260 may include at least one clutch feature that controls relative rotation between the driving plate 272 and spool 274. In one example, the clutch features include a spring biased follower 284 and biasing member 285 carried by the spool 274, which is biased into a follower recess 283 in the driving plate 272. The follower 284 may selectively connect and release the driving plate 272 relative to the spool 274 based on a torque force applied between the driving plate 272 and spool 274. FIGS. 10A and 10B illustrate operation of the follower 284 between the driving plate 272 and spool 274 to provide a clutch operation. The driving plate 272 may include a plurality of follower recesses 283 sized to receive the follower 284 in different rotated positions.

Figure 11:
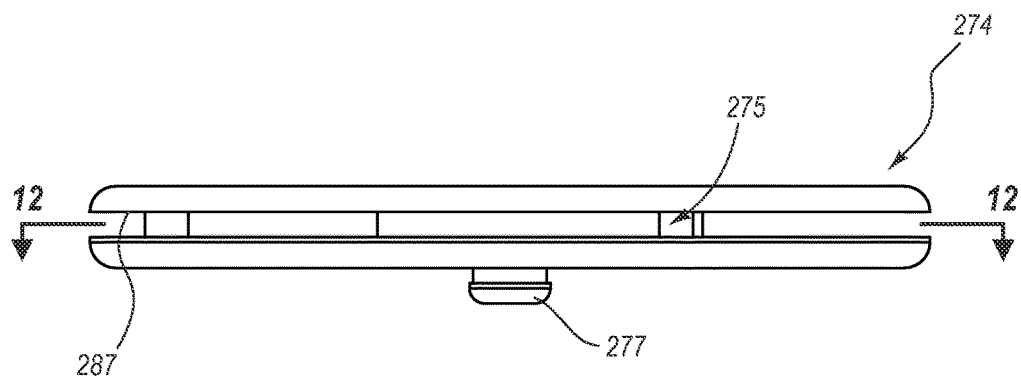
FIG. 11. is side view of the spool shown in FIG. 6.
Figure 12:
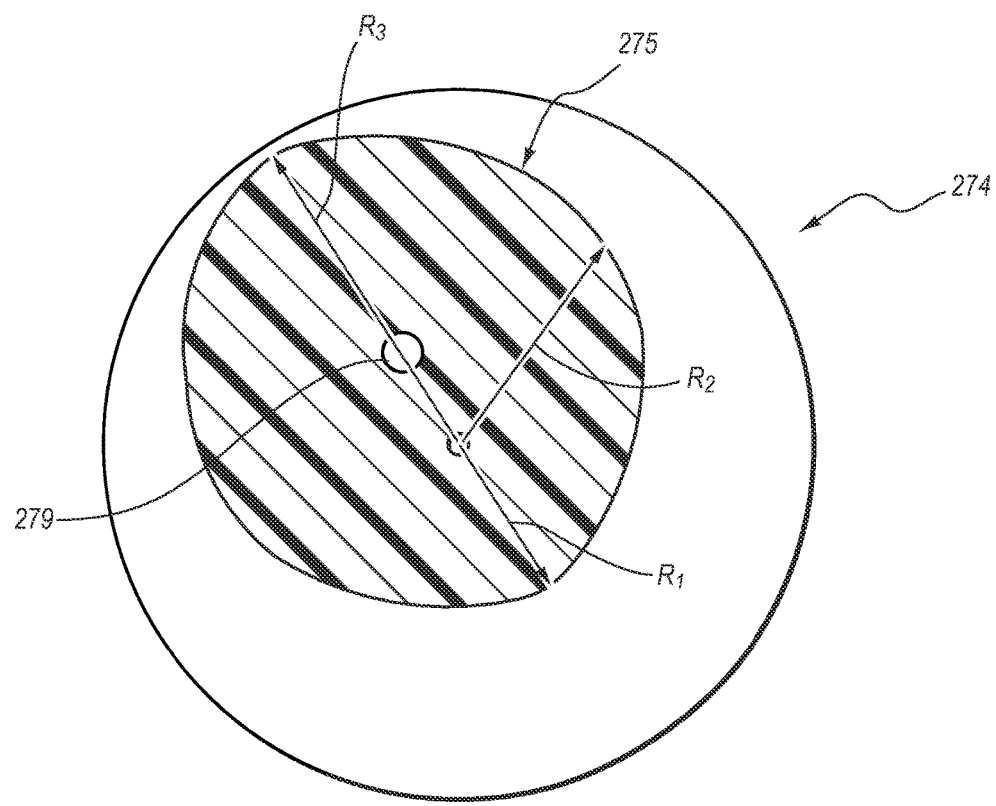
FIG. 12 is a cross-sectional view of the spool shown in FIG. 11 taken along cross-section indicators 12-12.
Figure 13:
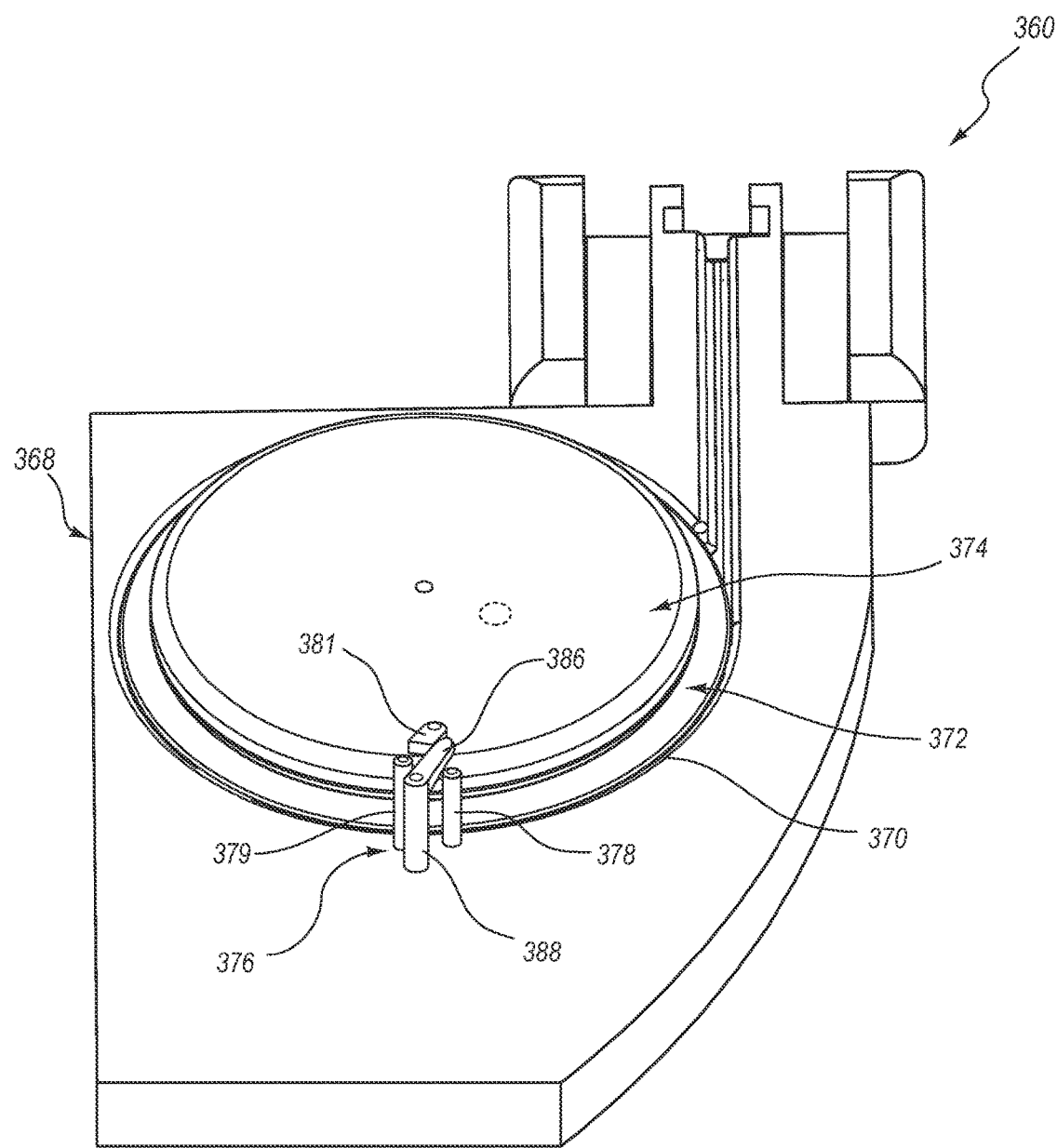
FIG. 13 is a top perspective view of another example driving mechanism according to the present disclosure.
Figure 14:
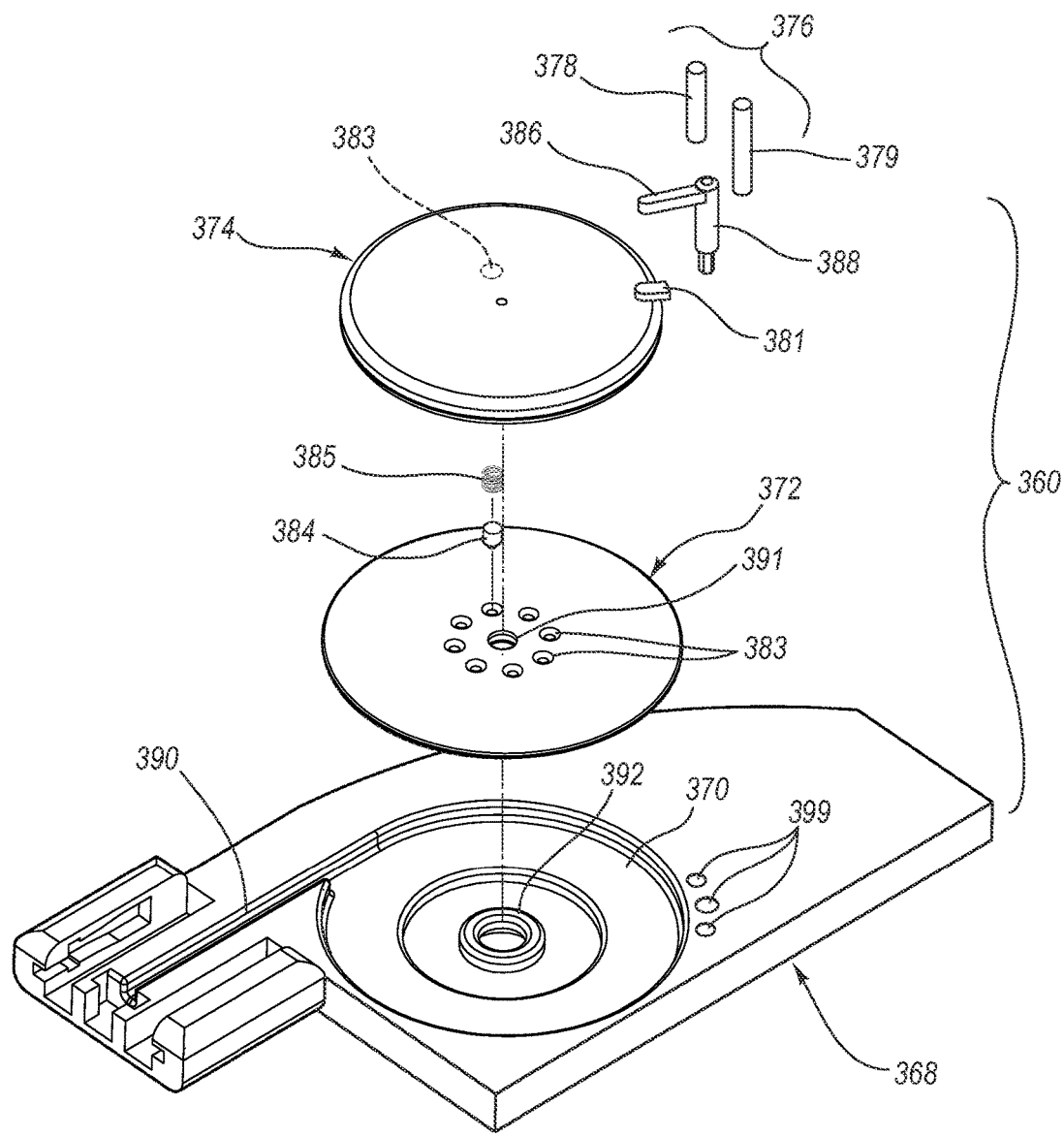
FIG. 14 is an exploded top perspective view of the driving mechanism of FIG. 13.
Figure 15:
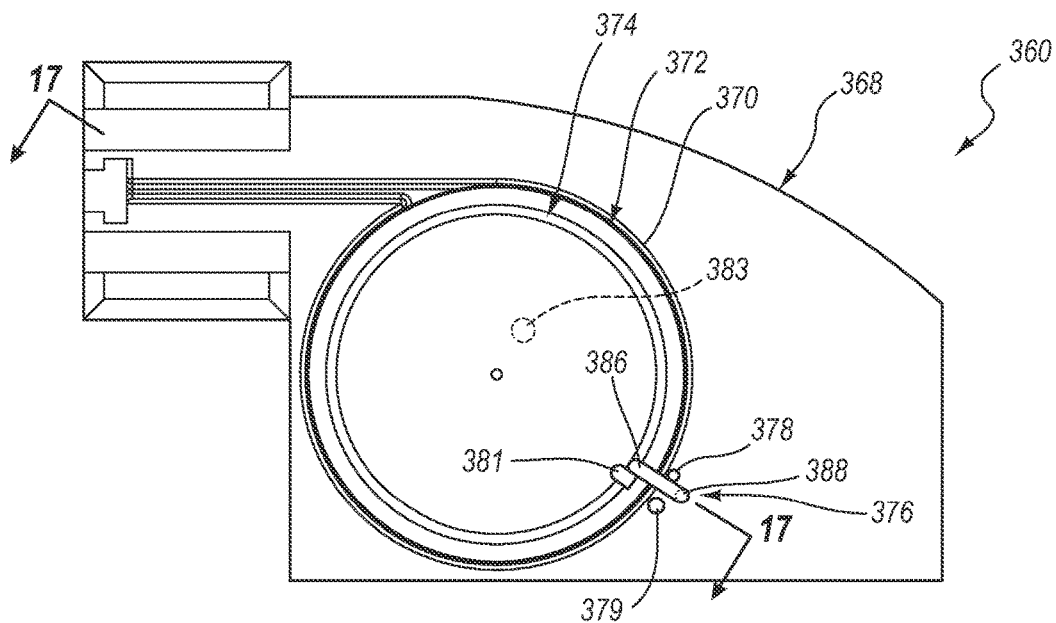
FIG. 15 is a top view of the driving mechanism of FIG. 13 in a stop position.
Figure 16:
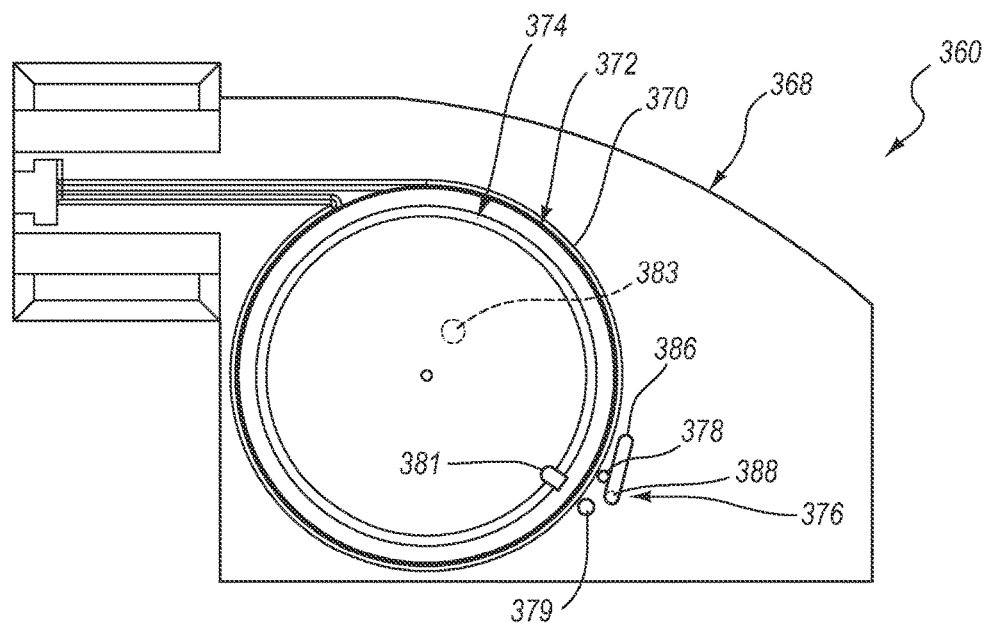
FIG. 16 is a top view of the driving mechanism of FIG. 13 in a release position.
Figure 17:
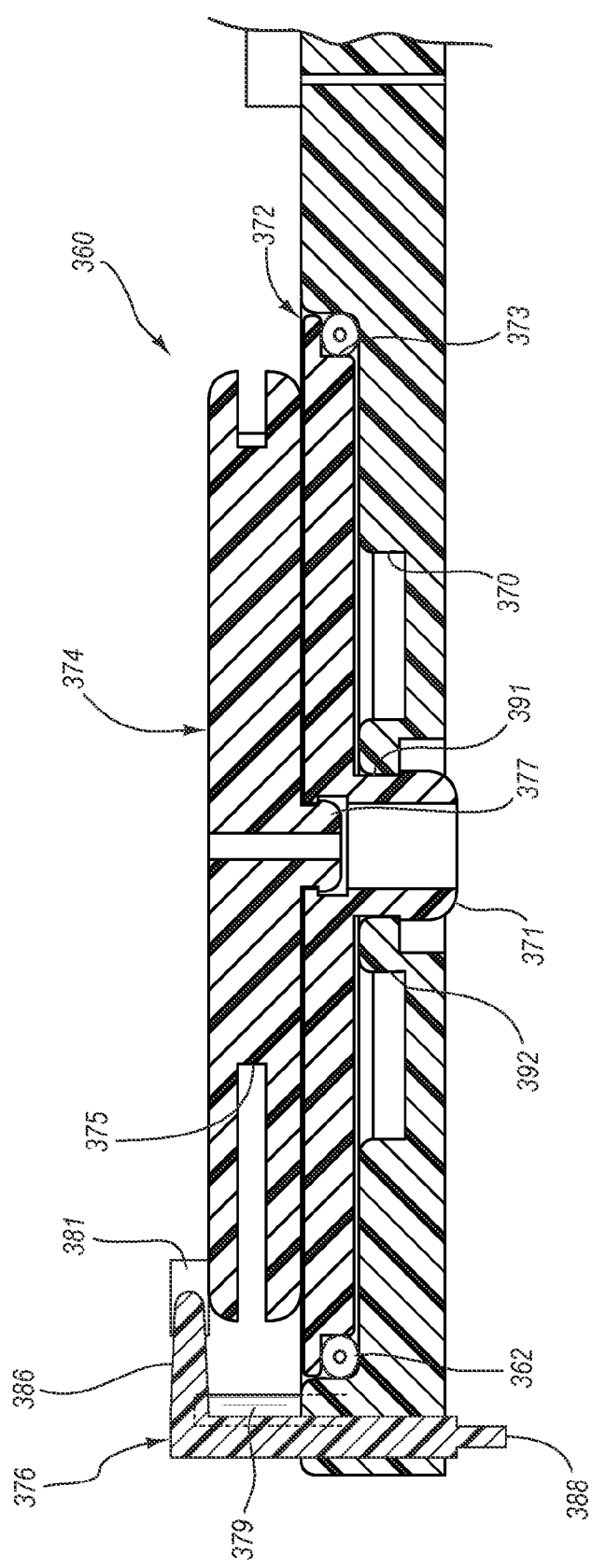
FIG. 17 is a cross-sectional view of the driving mechanism of FIG. 15 taken along cross-section indicators 17-17.

The spool 274 includes a cam surface portion 275, a connection feature 277, a pin recess 279, and a coil recess 287. The cam surface portion 275 may have a variable radius construction. FIGS. 11-12 illustrate the cam surface portion 275 having a different radiuses $R_1$, $R_2$, $R_3$ around the perimeter of the cam surface portion 275. When the suture 204 is wrapped around the cam surface portion 275 within the coil recess 287, unwinding of the suture 204 causes the spool 274 to rotate at a variable rate. The variable rotation rate of the spool 274 imposes a variable torsional force to the driving plate 272 and ultimately to the coil 262. Advancing the coil 262 and compaction tube 212 at a variable rate may assist in compacting the sealing plug 210 as the sealing plug 210 changes size and shape during compaction.

Figure 9A:
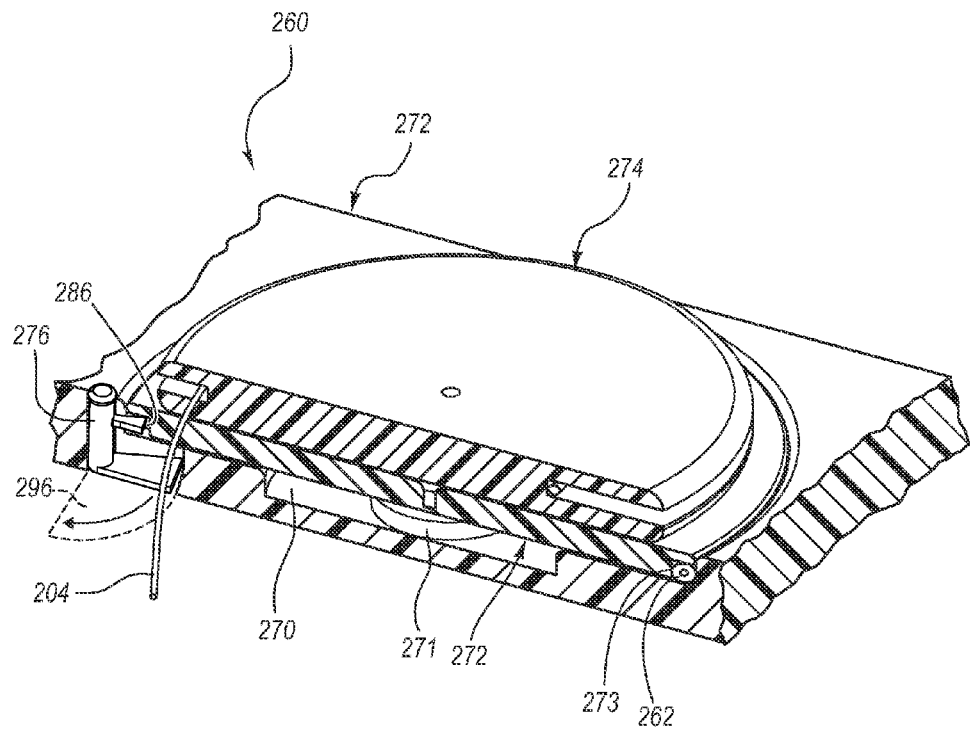
FIG. 9A is a cross-sectional view of the driving mechanism of FIG. 6 taken along cross-section indicators 9A-9A with a release member in a stop position.

The driving plate 272 and spool 274 may rotate upon unwinding of the suture 204 until the stop portion 286 of the release member 276 contacts the stop feature 281 (see FIG. 9A). Contact between the stop feature 281 and release member 276 resists further rotation of the driving plate 272 and spool 274. The operator may actuate the actuation portion 288 of the release member 276 to move the stop portion 286 away from a rotation path of the stop feature 281 (see FIG. 9B). The driving plate 272 and spool 274 may then further rotate to permit additional unwinding of the suture 204 from the spool 274. The variable radius construction of the cam surface portion 275 of the spool 274 may assist in unwinding the suture 204 without further compacting the sealing plug 210 with the compaction tube 212.

Figure 9B:
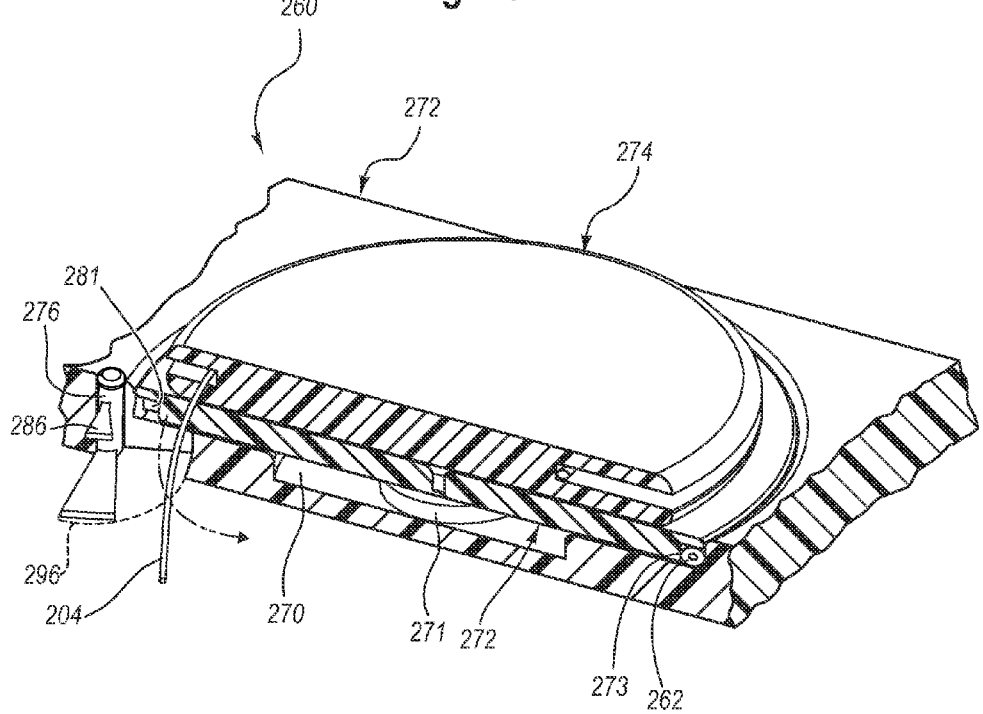
FIG. 9B shows the driving mechanism of FIG. 9A with the release member in a released position.

The release member 276 may be rotatable between the stop position shown in FIG. 9A and the release position shown in FIG. 9B. In other arrangements, the release member 276 may be axially movable between a stop position and a release position. In further arrangements, the release member 276 may pivot between a stop position and a release position.

The actuation portion 288 may include an attachment structure such as a slot or hex feature that promotes connection of the release member 276 to another actuation device that is accessible by the operator from outside of the housing 252. In some arrangements, the release member 276 is sized to extend outside of the housing 252.

Another embodiment of a automatic driving mechanism 360 is illustrated in FIGS. 13-17. The automatic driving mechanism 360 of FIGS. 13-17 may be used in place of and have similarities to the automatic driving mechanism 260 of FIGS. 5A-12.

An example operation of the embodiment of FIGS. 5A-12 is as follows. As the housing 252 of the closing device 200 is retracted from the percutaneous incision 219 as shown in FIG. 5E, the stowage detent 255 releases. The automatic driving mechanism 260 and carrier tube 202 may remain stationary and therefore float relative to the housing 252. The procedure sheath 216 is retracted as the housing 252 is withdrawn, exposing the distal end portion 207 of the carrier tube 202. The automatic driving mechanism 260 eventually contacts a stop (or, in some embodiments, the automatic driving mechanism is fixed), and further retraction causes the automatic driving mechanism 260 and carrier tube 202 to retract as well. As the automatic driving mechanism 260 retracts, the suture 204, which is threaded through the anchor 208, unwinds from and causes rotation of the spool 274. The spool 274 drives the driving plate 272 as it rotates via a coaxial connection there between.

As the driving plate 272 rotates, the coil 262 drives the compaction tube 212, or the coil 262 may be long enough to operate as a compaction tube itself. The compaction tube 212 compacts or compresses the sealing plug 210. The stop portion 286 of the release member 276 contacts the driving plate 272 to stop rotation of the driving plate 272 to stop compaction of the sealing plug 210. The operator then actuates the release member 276 from the stop position shown in FIG. 9A to the release position shown in FIG. 9B. With the release member 276 in the release position shown in FIG. 9B, the driving plate 272 and spool 274 may continue to rotate to release suture 204 without further compacting the sealing plug 210. The released suture 204 permits the operator to remove the closure device 200 from the percutaneous incision 219 to expose the suture 204 for cutting by the operator.

Moreover, when the sealing plug 210 has been sufficiently compacted, the automatic driving mechanism 260 may be disengaged by operating the release member 276 as discussed above, enabling further retraction of the closure device 200 without additional compaction. With the sealing plug 210 fully compacted, there may be little or no portion of the suture 204 extending outside of the tissue layer 230 and exposed to an operator. Therefore, it may be difficult for an operator to separate the sealing plug 210 and anchor 208 from the remainder of the closure device 200. In addition, too much retraction with the selectably automatic driving mechanism 260 enabled could potentially over compact the sealing plug 210 into the artery 228. Accordingly, the automatic driving mechanism 260 may be advantageously disabled by activating the release member 276. Activating the release member 276 allows the suture 204 to fully unwind from the spool 274 without further driving the compaction tube 212. Unwinding the spool 274 exposes a sufficient length of the suture 204 to allow an operator to easily cut the suture 204 and separate the sealing plug 210 and anchor 208 from the remainder of the closure device 200.

Referring now to FIGS. 13-17, another example automatic driving mechanism 360 is shown and described. The automatic driving mechanism 360 may include the same or similar features and operate similarly to the automatic driving mechanism 260 described above.

The automatic driving mechanism 360 includes a coil 362, a plate block 368, a driving plate 372, a spool 374, and a release member 376. Among other features, the plate block 368 includes a recess 370, a coil recess 390, and a hub 392. The driving plate 372 includes a connection feature 371, a connection recess 391, and a track or groove within which the coil 362 is positioned. The spool 374 includes a cam surface portion 375, a connection feature 377, and a follower recess 383. The spool 374 and driving plate 372 are releasably connected with a follower 384 that is positioned in the follower recess 383 and biased into one of the connection recesses 391 with a spring or biasing member 385.

The release member 376 includes a stop portion 386, an actuation portion 388, and a pair of release member stops 378, 379. The release member 376 is operable between a stop position (see FIG. 15) wherein the stop portion 386 contacts a stop feature 381 positioned on the spool 374, and a release position (see FIG. 16) wherein the stop portion 386 is moved out of the rotation path of the stop feature 381.

The release member stops 378, 379 may be sized and arranged to resist rotation of the stop portion 386 from the stop position to the release position until a threshold rotation force applied via the actuation portion 388 is exceeded. At least one of the release member stops 378, 379 may have a height that permits the stop portion 386 to move over a free end of the release member stop 378, 379. In some arrangements, the release member stops 378, 379 have different sizes and shapes, while in other arrangements the release member stops 378, 379 are identical in size and shape to permit movement of the stop portion 386 into the release position by rotation in either rotation direction.

The actuation portion 388 includes a hex-shaped proximal end (see FIG. 14) to promote a connection with another actuation device that is accessible by an operator outside the housing 252 of the closure device 200. The actuation portion 388 and release member stops 378, 379 may be supported on the plate block 368, such as by extending into support apertures 399 (see FIG. 14).

It will be understood by those of skill in the art having the benefit of this disclosure that the automatic driving mechanisms 260, 360 shown in FIGS. 5A-17 are exemplary in nature, and not limiting. Other configurations may be used to advance a coil within a channel to provide an automatic driving force to the sealing plug 210. Furthermore, many configurations are possible to limit rotation of a driving plate and/or spool and release the driving plate and/or spool to permit unwinding of the suture.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
   an anchor;
   a sealing plug;
   a filament slidingly attaching the sealing plug to the anchor;
   a compaction member assembly disposed adjacent to the sealing plug and structured and arranged to apply an axially directed compressive force to automatically compact the sealing plug toward the anchor, the compaction member assembly having a distal end and a proximal end;
   a spool having a portion of the filament wound thereon;
   a stop feature coupled to the spool;
   a driving plate connected to the spool and arranged to contact and apply a force to the proximal end of the compaction member assembly upon rotation of the driving plate to advance the compaction member assembly;
   a release member being operable from a first position contacting the stop feature to limit rotation of the spool, and a second position out of contact with the stop feature to permit rotation of the spool; and
   the release member being configured to rotate into and out of contact with the stop feature.

2. A tissue puncture closure device according to claim 1 wherein the compaction member assembly includes a compaction tube and a coil, the coil structured and arranged to apply an axially directed compressive force to the compaction tube to drive the compaction tube to automatically compact the sealing plug toward the anchor.

3. A tissue puncture closure device according to claim 2 wherein the driving plate includes a recess having a contoured shape, and at least a portion of the coil is positioned in the recess.

4. A tissue puncture closure device according to claim 1 wherein the spool includes a cam surface portion, a portion of the filament being wrapped around the cam surface portion, wherein unwinding the filament from the cam surface portion applies a variable rotation force to the driving plate.

5. A tissue puncture closure device according to claim 1 wherein the stop feature is a protrusion extending from the spool.

6. A tissue puncture closure device according to claim 1 wherein the compaction member assembly includes a compaction tube and a coil member arranged end-to-end, the compaction tube defining the distal end of the compaction member assembly and the coil member defining the proximal end of the compaction member assembly.

7. A tissue puncture closure device according to claim 1 wherein the stop feature is mounted to the driving plate, and the driving plate is connected to the spool.

8. A tissue puncture closure device according to claim 1 further comprising a release member stop configured to hold the release member in the first position.

9. A tissue puncture closure device according to claim 1 further comprising a housing sized to enclose the spool and driving plate, wherein the release member is operable from outside of the housing.

10. A tissue puncture closure device for partial insertion into and sealing of a tissue puncture in an internal tissue wall accessible through a percutaneous incision, comprising:
    an anchor for disposition on a distal side of the internal tissue wall;
    a sealing plug for disposition on a proximal side of the internal tissue wall;

a filament connected to and anchored at a distal end to the anchor and sealing plug for slideably cinching the anchor and sealing plug together about the tissue puncture, wherein the sealing plug is slideably disposed on the filament proximal to the anchor;

a compaction assembly disposed on the filament and arranged to compact the sealing plug along the filament distally towards the anchor;

a storage spool onto which a proximal end of the filament is wound;

a release member configured to resist rotation of the storage spool after partial unwinding of the filament from the storage spool, and operable into a release position that permits further unwinding of the filament from the storage spool without further compacting the sealing plug;

a housing within which the storage spool is housed; and the release member including a first portion that extends outside of the housing and a second portion that rotates into and out of contact with the storage spool.

11. A tissue puncture closure device of claim 10 further comprising a driving plate connected to and arranged coaxially with the storage spool, the driving plate configured to contact the compaction assembly to advance the compaction assembly.

12. A tissue puncture closure device of claim 11 wherein the driving plate includes a stop feature arranged to contact the release member.

13. A tissue puncture closure device of claim 10 wherein the storage spool includes a stop feature arranged to contact the release member, the stop feature protruding from a surface of the storage spool.

14. A tissue puncture closure device of claim 10 wherein the storage spool includes a cam surface portion about which the proximal end of the filament is wound, the storage spool applying a variable rotational force to the compaction assembly when the filament unwinds from the cam surface portion.

15. A method of sealing a tissue puncture in an internal tissue wall of a vessel accessible through a percutaneous incision, the method comprising:

providing a closure device having an anchor, a sealing plug, a filament slidingly attaching the sealing plug to the anchor, a compaction member assembly, a spool having a portion of the filament wound thereon, a driving plate, and a release member, a distal end of the compaction member assembly being disposed adjacent to the sealing plug, a proximal end of the compaction member assembly being in contact with the driving plate, and the driving plate being connected to the spool;

inserting the anchor through the tissue puncture;

withdrawing the closure device from the tissue puncture with the anchor positioned within the vessel, wherein withdrawing the closure device rotates the spool into contact with the release member, and rotating the spool rotates the driving plate to drive the compaction member assembly and compact the sealing plug toward the anchor;

actuating the release member to remove the release member from contact with the spool to permit further rotation of the spool without further compacting of the sealing plug toward the anchor; and the spool includes a stop protrusion, and the actuating of the release member includes rotating the release member into and out of contact with the stop protrusion.

16. A method according to claim 15 wherein rotating the spool into contact with the release member provide a tactile indicator to an operator of the closure device that compacting of the sealing plug is complete.

17. A method according to claim 15 wherein actuating the release member includes rotating the release member about an axis arranged perpendicular to a direction of compacting the sealing plug toward the anchor.

* * * * *